(12) United States Patent
Krause et al.

(10) Patent No.: US 9,808,867 B2
(45) Date of Patent: Nov. 7, 2017

(54) FLEXIBLE SHAFT FOR HOLDING A TOOL OF ROTARY DRIVEN MOTION

(71) Applicants: William R. Krause, Charlottesville, VA (US); Garland Edwards, Midlothian, VA (US)

(72) Inventors: William R. Krause, Charlottesville, VA (US); Garland Edwards, Midlothian, VA (US)

(73) Assignee: Flex Technology, Inc., Charlottesville, VA (US)

( * ) Notice: Subject to any disclaimer, the term of this patent is extended or adjusted under 35 U.S.C. 154(b) by 253 days.

(21) Appl. No.: 14/840,185

(22) Filed: Aug. 31, 2015

(65) Prior Publication Data

US 2017/0056979 A1   Mar. 2, 2017

(51) Int. Cl.
| | | |
|---|---|---|
| *B23B 45/00* | (2006.01) | |
| *B25B 23/00* | (2006.01) | |
| *A61B 17/16* | (2006.01) | |
| *B25B 15/02* | (2006.01) | |

(52) U.S. Cl.
CPC .......... *B23B 45/005* (2013.01); *A61B 17/162* (2013.01); *B25B 15/02* (2013.01); *B25B 23/0021* (2013.01); *B23B 2260/068* (2013.01)

(58) Field of Classification Search
CPC ........ B25G 1/025; B25G 1/063; B25G 1/005; B25B 15/02; B25B 23/0021
See application file for complete search history.

(56) References Cited

U.S. PATENT DOCUMENTS

| | | | | |
|---|---|---|---|---|
| 1,871,528 | A | | 8/1932 | Emmet |
| 2,704,005 | A | * | 3/1955 | Clayson ............... B25B 13/481 464/57 |
| 3,100,335 | A | * | 8/1963 | Lea ..................... B25B 27/0057 29/221.5 |
| 3,203,285 | A | * | 8/1965 | Schmidt ................ B25G 1/025 29/425 |
| 4,876,929 | A | * | 10/1989 | Kozak ................... B25B 13/481 81/177.6 |
| 5,464,407 | A | * | 11/1995 | McGuire ................ A61B 17/15 606/104 |
| 5,820,464 | A | | 1/1998 | Parlato |
| 6,053,922 | A | | 4/2000 | Krause |
| 6,283,973 | B1 | | 9/2001 | Hubbard et al. |
| 6,447,518 | B1 | | 9/2002 | Krause |
| 6,862,958 | B2 | * | 3/2005 | Schade ............... B25B 23/0021 403/223 |

(Continued)

FOREIGN PATENT DOCUMENTS

EP        0451932 A1    10/1991

*Primary Examiner* — David B Thomas
(74) *Attorney, Agent, or Firm* — Kimberly O. Snead; Sheldon H. Parker

(57) ABSTRACT

A tool having a flexible shaft, a first end and, a second end and capable of being bent about its axis. The tool transfers rotary motion from a device to tool. The shaft, manufactured from a rigid material, has at least one flexible segment, each flexible segment have at least one sinuous slot ascending in a helical path. With multiple segments, the helical path of the slots can be opposite or the same. With one or more segments having multiple slots, the slots can be parallel or have opposite ascensions, thereby crossing one another. The helical paths can vary within each segment or from segment to segment.

43 Claims, 29 Drawing Sheets

(56) References Cited

U.S. PATENT DOCUMENTS

| | | | | |
|---|---|---|---|---|
| 6,952,986 | B2* | 10/2005 | Fu | B25B 23/0021 |
| | | | | 403/157 |
| 8,117,950 | B2* | 2/2012 | Kozak | B23B 45/005 |
| | | | | 81/177.6 |
| 8,789,447 | B2* | 7/2014 | Kozak | B23B 45/005 |
| | | | | 81/177.6 |
| 9,492,167 | B2* | 11/2016 | Shelton, IV | A61B 17/068 |
| 9,545,252 | B2* | 1/2017 | Howard | A61B 17/0401 |
| 2008/0178712 | A1* | 7/2008 | Brown | B25B 15/02 |
| | | | | 81/450 |
| 2012/0132038 | A1* | 5/2012 | Lefler | B25B 13/481 |
| | | | | 81/177.6 |
| 2014/0283657 | A1* | 9/2014 | Kozak | B23B 45/005 |
| | | | | 81/177.6 |
| 2015/0343614 | A1* | 12/2015 | Hassler | B25B 13/483 |
| | | | | 81/124.7 |

* cited by examiner

Prior Art

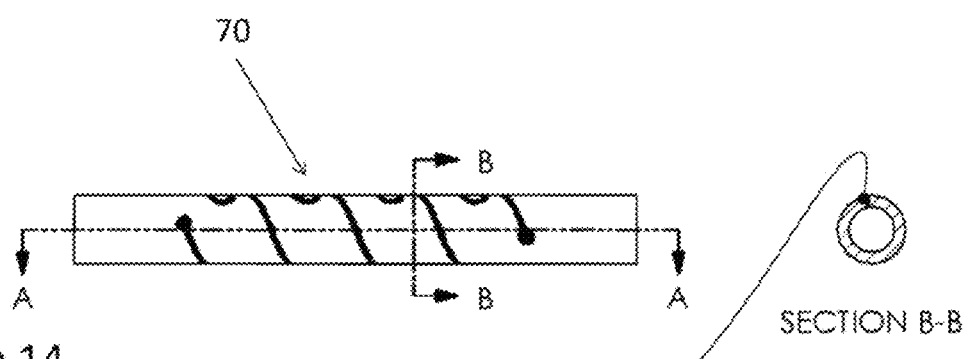
Figure 14
Figure 16 SECTION B-B
Figure 15 SECTION A-A

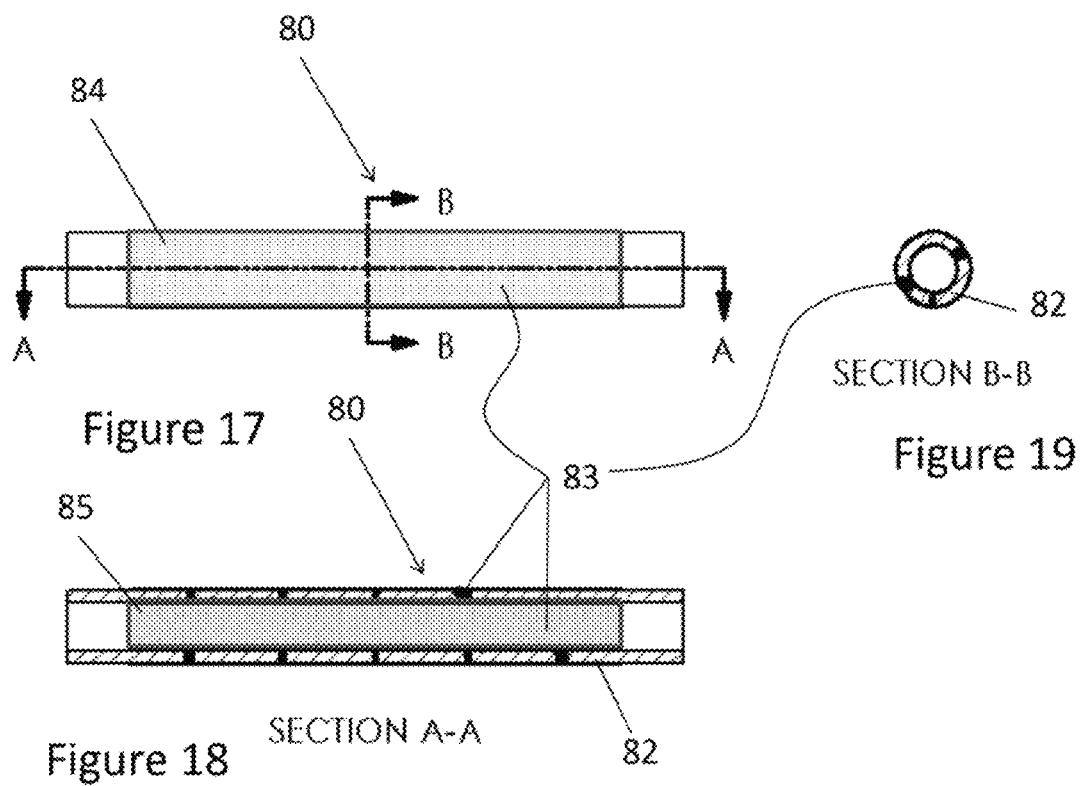

Figure 21 SECTION A-A

Figure 22 SECTION B-B

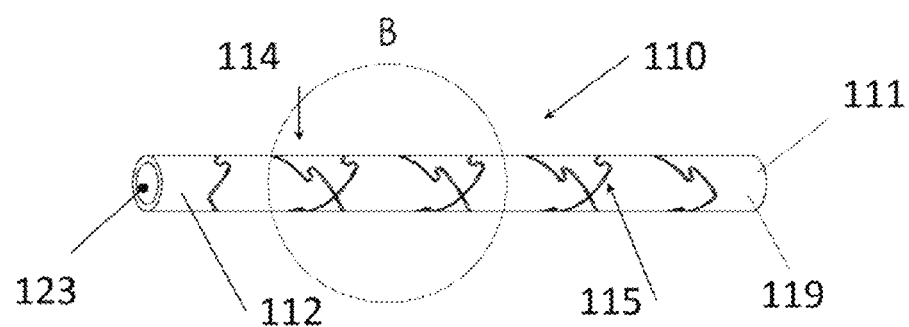
Figure 25
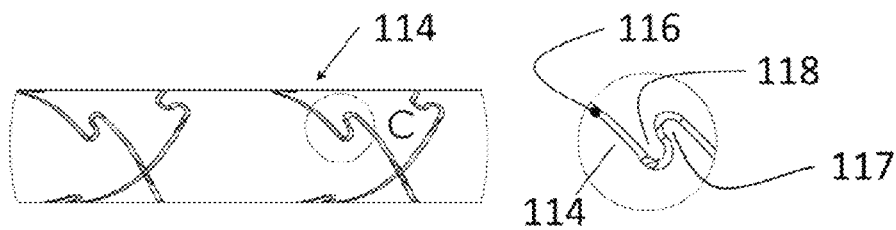
Figure 26   DETAIL B
Figure 27   DETAIL C

DETAIL E

Figure 36 SECTION B-B

SECTION A-A

FLEXIBLE SHAFT FOR HOLDING A TOOL OF ROTARY DRIVEN MOTION

FIELD OF INVENTION

This invention relates to flexible turning devices which are used for applying torque from a manual handle or motor to an attachment or tip that inserts into another device. The invention encompasses flexible screwdrivers, flexible drills, flexible reamers, flexible power extensions and other related turning devices.

DESCRIPTION OF THE RELATED ART

A screwdriver is a tool, manual or powered, for turning (driving or removing) screws. A typical simple screwdriver has a handle and a shaft, and a tip that the user inserts into the screw head to turn it. The shaft is usually made of tough steel to resist bending or twisting. The tip may be hardened to resist wear, treated with a dark tip coating for improved visual contrast between tip and screw—or ridged or treated for additional 'grip'. Handles are typically wood, metal, or plastic and usually hexagonal, square, or oval in cross-section to improve grip and prevent the tool from rolling when set down. Some manual screwdrivers have interchangeable tips that fit into a socket on the end of the shaft and are held in mechanically or magnetically.

A flexible shaft screwdriver, as illustrated in FIG. 1A has a shaft that is flexible to allow it to work around corners and in other spots that a regular screwdriver can't reach. The prior art tools have a flexible shaft comprised of wire wound in a helical fashion as seen in a coiled spring, an alloy steel blade or a socket for an interchangeable tip, and a handle. The prior art flexible shaft is comprised of a plurality of concentric coiled springs in a tightly wound adjacent relationship extending between the two ends. When such a shaft is twisted in the same direction as its winding, the top outer layer of the shaft compresses and tightens down (tighten outer layer: TOL) on the rest of the shaft. When the flexible shaft is twisted in the direction opposite to its outer winding, the outer wound wires loosen (loosen outer layer: LOL) and open up. As a rule, a flexible shaft operated in the TOL direction performs better than do those operated in the LOL direction.

A screwdriver is classified by its tip, which is shaped to fit the driving surfaces-slots, grooves, recesses, etc.—on the corresponding screw head. Proper use requires that the screwdriver's tip engage the head of a screw of the same size and type designation as the screwdriver tip. Screwdriver tips are available in a wide variety of types and sizes. The two most common are the simple 'blade'-type for slotted screws, and Phillips.

Flexible extension shafts, illustrated in FIG. 1B are also well known in the prior art, typically comprising a base configured to be received in the drive chuck of a standard ratchet, screwdriver, etc., a flexible shaft and a chuck adaptable to fit into a chuck or receive a standard or custom tool bit. The effect is to extend the reach of the tool by about the length of the flexible extension member. At the same time, the flexibility of the extension member allows a tool to perform a function in what might be otherwise an unreachable place, for example inside an item of machinery. Flexible, extension drills are tools with a drill bit at the flexible extension member to allow the drilling of holes within a structure that is inaccessible using a straight drill bit such as within residential and commercial building construction for the purpose of running extended wiring and cabling throughout the building. As with the flexible segment of the previously described flexible screwdriver, the extended length drill bits are presently wire wound constructs.

A reamer is a type of rotary cutting tool used in many industries to enlarge a previously formed hole. Precision reamers are designed to enlarge the size of a previously formed hole by a small amount but with a high degree of accuracy to leave smooth sides. There are also non-precision reamers which are used for more basic enlargement of holes or for removing burrs. The process of enlarging the hole is called reaming. There are many different types of reamers designed for use as a hand tool, attached to a hand power unit or in a machine tool, such as a milling machine or drill press. Flexible reamers are used to enlarge the inside diameter of a curved tube or a curved hole within a structure or device.

Extension drill bits are longer length high speed steel drill bits that can reach into areas that are difficult to access with standard length drill bits. Typically the length ranges from 15 cm (6 in) to 45 cm (18 inches) in length and with a range of shaft diameters from 1.0 mm (³⁄₁₆ in) to 25 mm (1 in) in shaft diameter. In addition, the extension head may be in the shape of a reamer head for the enlargement of an existing hole.

The application of flexible turn ing devices encompasses a broad spectrum of industries, included, but not limited to, manufacturing, construction, mining, transportation, agriculture, aviation, automotive, and medical. Flexible fastening devices, either like screwdrivers and or flexible extensions, have the characteristics in which the cylindrical central portion of the device is bendable about the longitudinal length.

A common characteristic of all the current, prior art flexible screwdrivers, extension bits and flexible drills commercially available is that the shaft connecting the leading end to the trailing end is a wire wound structure as described in U.S. Pat. Nos. 1,871,528 A and 5,820,464 A. A deficiency of this type of wire wound flexible shaft is that the shaft has a preferred rotational direction, usually in the TOL direction to achieve maximum torque. In the reverse, LOL direction, the allowable torque before failure is typically 50 to 60% of the driving torque. Thus the removal of a screw or bolt using a flexible shaft device is severely compromised. Another deficiency is the axial stretch when rotated or the tendency of a shaft to get longer or shorter in length when a torsional load is applied.

SUMMARY OF THE INVENTION

The disclosed flexible turn ing device provides a device that will allow for the curvature of the tool relative to the longitudinal axis of the device. The flexible shaft for use with a tool is manufactured from a rigid material with a rigid first end capable of receiving an instrument to impart rotary motion and a rigid second end dimensioned to receive a tool. The body of the shaft, between the rigid first and second ends is hollow with an outer surface and inner cavity. At least one flexible segment, each with proximal and distal segment ends, each contain at least one sinuous slot. The segments can be separated from sequential segments by a rigid section or they can be continuous with adjacent segments. The sinuous slots have a width, a depth from the outer surface to the inner cavity, and start points and end points at predetermined distances from the first end. There are circular ends at the start point and end point of each sinuous slot. The width of the slots is about 0.005 to about 0.25 inches, or about 2.5% to about 20% of a diameter of the body and contributes to the flexibility of the shaft. The sinuous path forms interlocking teeth that, when transferring rotary motion, interlock with adjacent teeth while the body is unbent or bent about an axis. The instrument used to initiate rotary motion can be manual, such as a handle, or powered. The tool can be, among other tools, a reamer, screwdriver or extension bar.

A number of slot configurations can be used with one or more multiple configurations per shaft. One such configuration is a single slot ascending a single segment or a single slot ascending multiple segments, all slots going the same direction. Another configuration is a single slot ascending a single segment or a single slot ascending multiple segments, with the slots ascending in a clockwise direction in one segment and counterclockwise direction in a subsequent segment, alternating by segment. Two slots can also be used in one or more of the segments in the shaft. The segments can also have two slots with the starting and ending points spaced from one another. The slot can ascend in the same direction or opposite directions. When ascending in the same direction, the slots are spaced from one another and, approximately parallel. When ascending in opposite directions, the slots will cross one another along the helical path. The segments with double slots can be mixed with single slot segments or all segments can have double slots. The patterns of the slots can also change both within the segments as well as from segment to segment.

The sinuous slots can have a helical angle of about 30 to 85 degrees from the longitudinal axis and preferably have a helical angle of about 45 to 75 degrees from the longitudinal axis. Each slot can have a helical angle different from the helical angle of another slot with the same segment or other segments in the shaft. The slots have a depth that can be cut perpendicular to a plane tangent to the outer surface of the body or can be cut at an angle with a plane tangent to the outer surface to form an undercut. When cut at an angle it is in the range of about one to about 75 degrees and preferably about 30 to about 45 degrees.

The slots can also have an elastomeric material applied to one or more of the interior cavity, slot, exterior surface or inner surface.

To use the flexible shaft, an instrument to transmit the rotary motion is attached to a first end and a tool to the second end. The tool is placed over the element to be rotated and the instrument rotated, transmitting the rotary motion to the tool.

The disclosed flexible turning device is an application specific improvement over the flexible shaft technology as taught by Krause et al in U.S. Pat. Nos. 6,053,922 and 6,447,518 by imparting a serpentine, helical slot along a segment or segments of the component to form a flexible shaft. Preferably, the flexible shaft is formed by laser cutting an elongated tubular member of substantial wall thickness, to form the slot around and along the tubular member. Preferably, the sinusoidal wave forms dovetail-like teeth, which have a narrow base region and an anterior region that is wider than the base region. Thus, adjacent and opposing teeth interlock. The teeth can have a configuration as illustrated in U.S. Pat. No. 6,053,922, the disclosure of which is incorporated herein by reference, as though recited in detail. Additional configurations which prevent or limit excessive rotation are also illustrated in U.S. Pat. No. 6,053,922, the disclosure of which is incorporated herein by reference, as though recited in detail. In addition, the slot about the helical path can be interrupted with a saw tooth or zig-zag configuration. In this configuration under torque or bending, the flat surfaces of the slot, as opposed to interlocking teeth will contact preventing excessive rotation or bending.

The flexible segment of the turning device is manufactured from a rigid or semi rigid material and has a body with a length and a diameter, multiple segments and a length to diameter aspect of at least 2.

The central segment has at least one helical, sinuous slot to form a flexible segment. When multiple segments have helical slots, the slots can have a different pattern than, and spaced from, adjacent slots. In addition, the slots can ascend in opposite rotational directions either within the same segment or different segments. The space between slots is inflexible. As shown in FIG. 2A the helical angle 212 of the slots 202 range from about 5 degrees to about 75 degrees and the ratio of the amplitude 218 of sinuous path to the helix rise 210 is in the range from greater than 0.1 to about 0.8.

Advantageously, the slot is cut at an angle normal to the shaft using a computer controlled cutting technique such as laser cutting, water jet cutting, milling or other means. Additionally, this slot may be cut at an angle to the normal so as to provide an undercut slot having a preferred angle in the range up to ±45 degrees from the normal. The sinuous pattern is about 1 to about 10 or more cycles per longitudinal revolution dependent upon the sinuous pattern, amplitude of the sinuous pattern and the width of the slot. The sinuous pattern may be a repeating pattern or could be a random pattern about the helical path.

A plurality of slots can be employed thereby increasing the flexibility of the component, relative to a shaft having a single slot of identical pattern. The serpentine path forms a plurality of teeth and complimentary recesses on opposite sides of the slot. The slot has sufficient width to form an unbound joint permitting limited movement in any direction between the teeth and the recesses, thereby providing limited flexibility in all directions upon application of tensile, compressive, and/or torsion forces to said component. In a similar manner the slot can have increased width in one direction compared to another direction thus providing increased flexibility in one direction. The slot can be as small as 0.001 inches and as large as 0.100 inches or greater dependent upon the diameter of the shaft and sinuous pattern.

The flexible segment can have different degrees of flexibility along the length of the shaft that is achieved by having the pitch of the helical slot vary along the length of the shaft. The varied flexibility corresponds to the variation in the pitch of the helical slot. The helical path, which can be varied along the length of the shaft to produce correspondingly varied flexibility, can have a helix angle in the range of about 5 degrees to about 75 degrees, depending upon the desired degree of flexibility. Alternatively, the width of the helical slot can vary along the length of the shaft to provide the varied flexibility. The rigidity of the flexible shaft can be achieved through the design of the slot pattern, thereby enabling the use of thinner walls than would otherwise be require to produce equivalent rigidity. In a preferred embodiment, the ratio of the amplitude of the serpentine path to the pitch of the slot is in the range from greater than 0.1 to about 0.8. The flexibility of the device will be dictated by the application with respect to the inaccessibility of the item needed to be turned. For example, a mechanic requiring to tighten or loosen a bolt deep in the engine compartment of an automobile may choose a very flexible extension shaft to reach the bolt while for a bolt in a relatively easily accessible area, the mechanic may choose a stiffer extension shaft.

In one embodiment the slot can be filled with a resilient material, partially or entirely along the path of the slot. The resilient material can be an elastomer compound which can be of sufficient thickness to fill the slot and to encapsulate the entire shaft thus forming an elastomer enclosed member or any other elastomeric material appropriate for the end use. The elastomer can be a resilient material such as a urethane or a silicone compound. The rigidity of the flexible shaft can be further achieved or varied through the use of filler material having different stiffness properties, thereby enabling the use of thinner walls than would otherwise be required to produce equivalent rigidity. The use of an elastomer is disclosed in the flexible shaft technology as taught by Krause et al in U.S. Pat. Nos. 6,053,922 and 6,447,518, which are incorporated herein as though recited in full.

BRIEF DESCRIPTION OF THE DRAWINGS

Examples of the invention are illustrated in the drawings herewith. All of the figures are drawn on an oversized scale, and like structure in different figures bears like reference numerals.

FIG. 14 a horizontal view of the flexible shaft 70 of FIG. 13 showing the location of Sections A-A and B-B, FIG. 15 is a longitudinal, cross sectional view of the flexible shaft of FIGS. 13 and 14 through the cross section A-A in longitudinal axis of FIG. 14, showing general pattern of the serpentine slots along the length of the rod and showing the elastomer material within the slot in accordance with the invention;

FIG. 16 is a view of section B-B in FIG. 14 showing the elastomer material within the slot in accordance with the invention.

FIG. 17 is an illustration of the flexible shaft 80 with an elastomeric coating covering the flexible region of shaft 80.

FIG. 18 is the sectional view of Section A-A in FIG. 17;

FIG. 19 is a the sectional view of Section B-B in FIG. 18 showing the elastomer coating the interior and exterior surface of the shaft and within the slot;

FIG. 21 is a sectional view of the Section A-A showing complete filling of the slot and interior cavity of the shaft in FIG. 20 in accordance with the invention;

FIG. 22 is a cross sectional view of the Section B-B of FIG. 20 showing complete filling of the slot and interior cavity of the shaft in FIG. 20 in accordance with the invention;

FIG. 25 is the horizontal view of the double helix pattern flexible shaft in FIG. 23;

FIG. 26 is a magnified view of the area B of FIG. 25 in accordance with the invention;

FIG. 27 is a magnified view of the area C of FIG. 26 in accordance with the invention;

FIG. 36 is a cross sectional illustration though the longitudinal axis B-B in FIG. 35 in accordance with the invention;

DESCRIPTION OF THE PREFERRED EMBODIMENT

Definitions

Figure 1A:
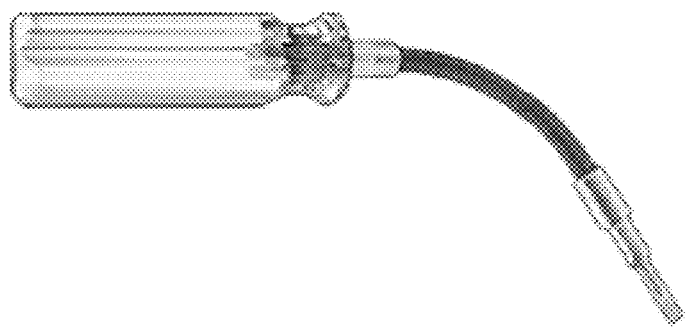
FIG. 1A shows prior art of a wire wound flexible screw driver.

For the purposes herein the term "flexible turning device" relates to devices which are used to transmit torque or power in a curvilinear manner. The device is used for applying torque from a manual handle or motor to an attachment or tip that transmits the rotational motion. The invention encompasses flexible screwdrivers, flexible drills, flexible reamers, flexible power extensions and other related turning devices. Typically these tools are relatively small having a flexible portion with a diameter in the range of 0.04 inches (1 mm) to up to 1 inch (25.4 mm). An example of a 0.04 inch flexible device could be, but not limited to, a flexible jeweler's screwdriver where as a 1 inch extension shaft may be for used on large bolts.

For the purposes herein the terms "slit" and "slot" are used interchangeably, consistent with their definitions, as follows:
  slot—n.
    1. A narrow opening; a groove or slit: a slot for coins in a vending machine; a mail slot.
    2. A gap between a main and an auxiliary airfoil to provide space for airflow and facilitate the smooth passage of air over the wing.

For the purposes herein the term "pitch" as used herein is defined as:
  Pitch—n.
    1. The distance traveled by a machine screw in one revolution.
    2. The distance between two corresponding points on adjacent screw threads or gear teeth. (American Heritage Dictionary, 3rd Edition, Copyright 1994)

For the purposes herein the term "cycle" as used herein is defined as:
  Cycle—
    1. An interval of time during which a characteristic, often regularly repeated event or sequence of events occurs: Sunspots increase and decrease in intensity in an 11-year cycle.
    2a. A single complete execution of a periodically repeated phenomenon: A year constitutes a cycle of the seasons.
    2b. A periodically repeated sequence of events: cycle includes two halves of the sine-wave like undulation of the slot path. (American Heritage Dictionary, 3rd Edition, Copyright 1994)

For the purposes herein the term "amplitude" shall refer to the maximum absolute value of the periodically varying quantity of the slot.

For the purposes herein the term "serpentine" shall refer to:
  1. winding or turning one way and another <a serpentine road>.
  2. having a compound curve whose central curve is convex. (Merriam-Webster online dictionary)

For the purposes herein the term "sinuous" shall refer to:
  1. of a serpentine or wavy form: winding,
  2. marked by strong lithe movements. (Merriam-Webster online dictionary)

The terms sinuous and serpentine are used interchangeably herein.

For the purposes herein the term "helical", "helix" and "spiral" are used interchangeable and shall refer to:
  1a. winding around a center or pole and gradually receding from or approaching it <the spiral curve of a watch spring>
  1b. helical
  1c. spiral-bound <a spiral bound notebook>.
  2. of or relating to the advancement to higher levels through a series of cyclical movements. (Merriam-Webster online dictionary)

For the purposes herein the term "about" shall refer to plus or minus ten percent (10%).

For the purposes herein the term "approximate" shall refer to plus or minus ten percent (10%).

For the purposes herein the term "helix angle" 212 or "helical angle" shall refer to the angle, ϕ, between the overall helical path of the slot and the axis normal to the longitudinal axis of the shaft, as illustrated in FIG. 2. The helix angle, ϕ 212 can be found by unraveling the helix slot 202 from the shaft 200, FIG. 2, representing the section as a right triangle, and calculating the angle that is formed.

$$\phi 212 = \arctan(P/\pi D) \quad \text{Helix angle,}$$

where;
a. P is the pitch, lead or rise of the slot 214
b. D is the diameter of the shaft 216

For the purposes herein the term "slot angle" shall refer to the angle of the slot relative to a plane tangent to the longitudinal axis of the shaft.

For the purposes herein the term "frequency" shall refer to the number of times a specified phenomenon occurs within a specified interval:
  Frequency.
    1a. Number of repetitions of a complete sequence of values of a periodic function per unit variation of an independent variable.
    1b. Number of complete cycles of a periodic process occurring per unit time.
    1c. Number of repetitions per unit time of a complete waveform, as of an electric current. The number of times the cycles form a repetitive pattern in one unit of length is the frequency of the slot pattern. The number of cycles of the slot undulations superimposed upon the circumferential path which are present in one revolution around the shaft is referred to as the cycles per revolution. (American Heritage Dictionary, 3rd Edition, Copyright 1994).

Figure 3:
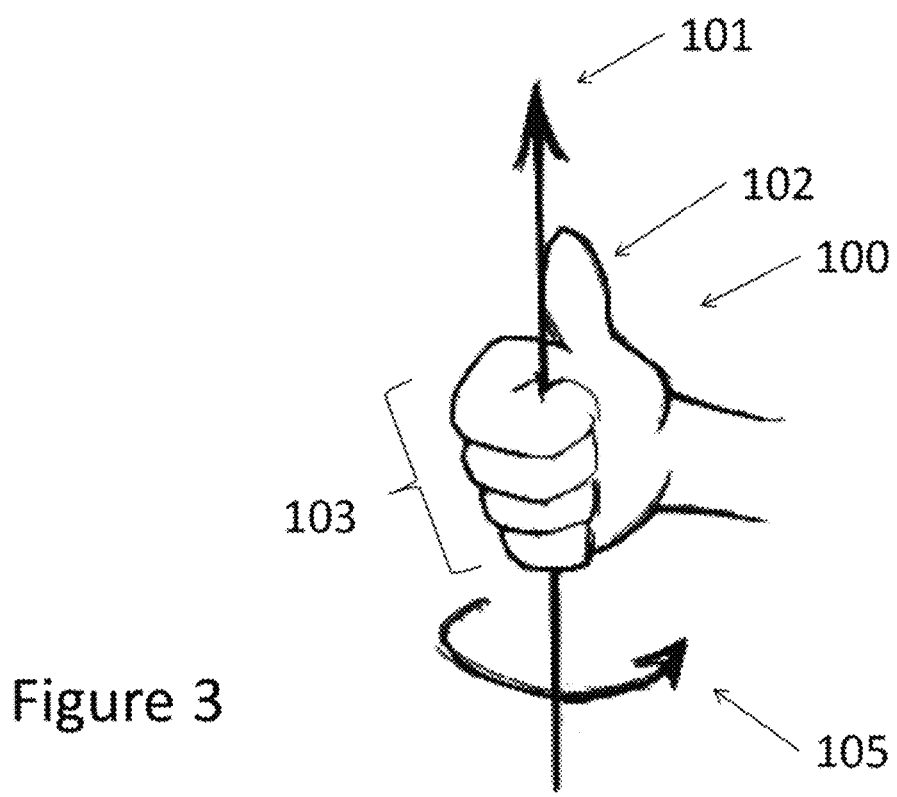
FIG. 3 is an illustration depicting the "Right Hand Rule" to define the rotation about an axis.

As used herein the term "Right Hand Rule" shall be used in the definition of the helical path for rotations is used to define the rotation about the shaft, FIG. 3. The direction of rotation is determined if the right hand 100 grasps an axis 101 of the shaft with the thumb 102 oriented in the direction of the shaft, fingers 103 will then curl in direction of positive rotation 105 for that axis which would correspond to a counter clockwise rotation about the axis if looking directly at the tip of the thumb. If the right hand's direction is reversed about the shaft, i.e. the thumb pointed down, a finger curl will be in the opposite or clockwise rotation.

As used herein the term "tool" shall refer to a device or implement used to carry out a particular function, task or purpose in any area of endeavor.

As used herein the term "shaft" and "element" shall be used interchangeably and refer to the bar used to support rotating pieces or to transmit power or motion by rotation, such as between a power drill and a bit tip, a surgical reamer tip and a rotational driver or a socket wrench and socket.

Glossary

| | |
|---|---|
| 110 | screwdriver |
| 12 | Handle |
| 14 | Flexible shaft |
| 16 | Screwdriver tip |
| 20 | Extension device |
| 22 | Drive end |
| 24 | Central flexible shaft |
| 24' | Flexible segment |
| 24" | Flexible segment |
| 26 | socket drive tip |
| 30 | Flexible reamer |
| 32 | Drive end |
| 33 | Reamer tip |
| 34 | Central flexible shaft |
| 34' | Distal segment |
| 34" | proximal segment |
| 35A | segment proximal end |
| 35B | segment distal end |
| 36 | Cutting flukes |
| 39 | Trailing segment |
| 40 | Flexible shaft |
| 41 | leading end segment |
| 42 | amplitude |
| 43 | pitch |
| 44 | Flexible section |
| 44' | Distal segment |
| 44" | Proximal segment |
| 45 | Interlocking teeth |
| 46 | Interlocking teeth |
| 47 | Helix angle |
| 48 | Serpentine slot |
| 48A | Slot depth |
| 49 | Slot gap width |
| 141 | Interior cavity |
| 50 | High helix flexible element |
| 51 | Outer surface |
| 52 | wall |
| 53 | Helical slot |
| 54 | Helical slot |
| 55 | Inner cavity of shaft |
| 56 | End of slot drill hole |
| 57 | Helix angle |
| 58 | Hollow tube |
| 70 | Flexible element with filler in slot |
| 72 | Slot |
| 73 | elastomeric material |
| 74 | Exterior surface |
| 75 | Interior surface |
| 76 | Interior cavity |
| 80 | Flexible element with filler in slot and covering interior and exterior surfaces |
| 82 | slot |
| 83 | elastomeric material |
| 84 | Exterior surface |
| 85 | Interior surface |
| 86 | Interior cavity |
| 90 | Flexible shaft with filler in slot and interior cavity and covering exterior surface |
| 92 | slot |
| 93 | elastomeric material |
| 94 | Exterior surface |
| 95 | Interior surface |
| 96 | Interior cavity |
| 100 | Right hand |
| 101 | Shaft axis |
| 102 | Right thumb |
| 103 | right fingers |
| 105 | Rotation direction |
| 110 | Double intersection helix shaft |
| 111 | Distal, far end of the shaft |
| 112 | Proximal, near end |
| 114 | Counter-clockwise sinuous helical slot |
| 115 | Clockwise sinuous helical slot |
| 116 | Gap in slot |
| 117 | Tooth in slot |
| 118 | Tooth in slot |
| 119 | Wall |
| Φ | Angle of slot 114 |
| β | Angle of slot 115 |
| Ω | Angle of slot to shaft exterior |
| 120 | Double segment, opposite helix flexible shaft |
| 121 | Proximal, near end |
| 122 | Distal, far end of the shaft |
| 123 | Interior cavity |
| 124 | Central flexible shaft |
| 124' | Flexible segment |
| 124" | Flexible segment |
| 125 | Clockwise sinuous slot |
| 126 | Counter-clockwise sinuous slot |
| 150 | Double segment, opposite helix flexible shaft |
| 151 | Near end |
| 152 | Far end |
| 153 | Interior cavity |
| 154 | Flexible segment |
| 154' | Flexible segment |
| 154" | Flexible segment |
| 155 | Helical slots |
| 156 | Helical slots |
| 230 | Double helix shaft |
| 231 | Proximal, near end |
| 232 | Distal, far end of the shaft |
| 233 | Interior cavity |
| 234 | Long segment of slot |
| 235 | First sinuous helical slot |
| 236 | Second sinuous slot |
| 237 | Near first slot hole |
| 237' | Far first slot hole |
| 238 | Near second slot hole |
| 238" | Far second slot hole |
| 200 | Flexible shaft section |
| 201 | proximal end of slot |
| 202 | Slot |
| 204 | Slot width |
| 206 | Cycle |
| 208 | Circumference |
| 210 | Helix rise |
| 212 | Helix Angle |
| 214 | Pitch |
| 215 | Longitudinal Axis |
| 216 | Diameter |
| 218 | Amplitude |
| 220 | Proximal Dovetail tooth |
| 222 | distal Dovetail tooth |
| 250 | shaft |
| 252 | slot |
| 300 | shaft |
| 302 | proximal slot |
| 304 | distal slot |
| 306 | turning point |
| 308' | distal segment |
| 308" | proximal segment |
| 340 | shaft |
| 342 | first proximal slot |
| 344 | second proximal slot |
| 346 | distal slot |

While the present invention will be described more fully hereinafter with reference to the accompanying drawings, in which particular embodiments and methods of implantation are shown, it is to be understood at the outset that persons skilled in the art can modify in light of the teachings herein, the invention described while achieving the functions and results of this invention.

Accordingly, the descriptions that follow are to be understood as illustrative and exemplary of specific structures, aspects and features within the broad scope of the present invention and not as limiting of such broad scope.

The present invention overcomes the deficiencies and problems evident in the prior art of wire wound devices as described herein above by combining the features as disclosed herein into an integral, longitudinally, laterally and torsional flexible segment of the tool. The principle advantage of the present invention, that of a serpentine or sinuous helical slot in the flexible segment of the device, provides a higher driving and reversal torque than traditional wire wound shafts as well as providing superior longitudinal extension of contraction during rotation.

The invention in one embodiment relates to a flexible device having one or more flexible segments within a section of the device created through the use of at least one sinuous helical slot formed in a segment of the device. In other embodiments, additional flexible segments also have at least one sinuous helical slot in either the same helical rotation and pattern or in an opposite rotation and/or different pattern. In another embodiment the flexible section or sections have a flexible segment that has at least one helical, sinuous slot within a section of the element that is embedded within a polymer or other flexible material so as to fill the slot with the flexible material as disclosed in U.S. Pat. Nos. 6,053,922 and 6,447,518 which are incorporated herein as though recited in full. In an additional embodiment the hollow flexible element encompasses a polymer or other flexible material within its central core without extending into the sinuous slot(s). Although only one or two slots are illustrated per segment, this is for illustration purposes only and any number of slots required to achieve the desired flexibility without compromising functionality can be used. A further embodiment the polymer or other flexible material within the central core of the flexible slotted segment extends radially outward through the sinuous slot(s). The flexible shaft can contains a polymer or other flexible material within the central core of the flexible segment that extends radially outward through the slot and encompasses the outer surface of the element and/or the flexible segment.

Accordingly, the descriptions that follow are to be understood as illustrative and exemplary of specific structures, aspects and features within the broad scope of the present invention and not as limiting of such broad scope.

Although the Krause patents noted heretofore teach a helical pattern, they cannot directly be applied to the flexible tool shaft. In both the '922 and '518 patent the preferred helical angle is less than 20 degrees, although in the '518 it is stated that in some applications the angle can be between 10 and 45 degrees. In the current teachings the helix angles are higher, with a range of 30 to 85 degrees and a preferred range of 45 to 75 degrees. With too low of an helical angle, when rotated in the direction of the serpentine slot, the shaft contacts or shortens and went rotated in the direction opposite to the serpentine slot, the shaft lengthens or elongates. Although the shortening and lengthening of the shaft in many applications provides no detriment, in some applications the shortening/lengthening action does not provide optimal results. To provide optimal results in those applications where the length of the shaft must have minimal longitudinal movement, a section of shaft, or multiple sections with the serpentine helical slot spiral in one direction and a second section, or multiple sections, rotated in the opposite direction. Another aspect of the invention is to have a double helix with one or more helix rotated in a clockwise direction, and a second or more helixes in a counterclockwise rotation within the same section of shaft. With the combination of clockwise and counter clockwise rotations, the elongation or contraction can be minimized.

Figure 1B:
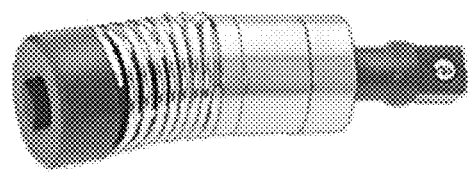
FIG. 1B illustrates a flexible socket extension.

FIGS. 1A and B show a prior art wire wound flexible screw driver, FIG. 1A, illustrates a side view of a flexible socket extension, and FIG. 1B a socket wrench flexible extender as sold by McMaster Carr, a commercial supply house. The applications for the flexible element are numerous and a few are discussed herein although additional applications will readily be known by those skilled in the art and the disclosed applications should not be considered to limit the scope of the invention.

Figure 2A:
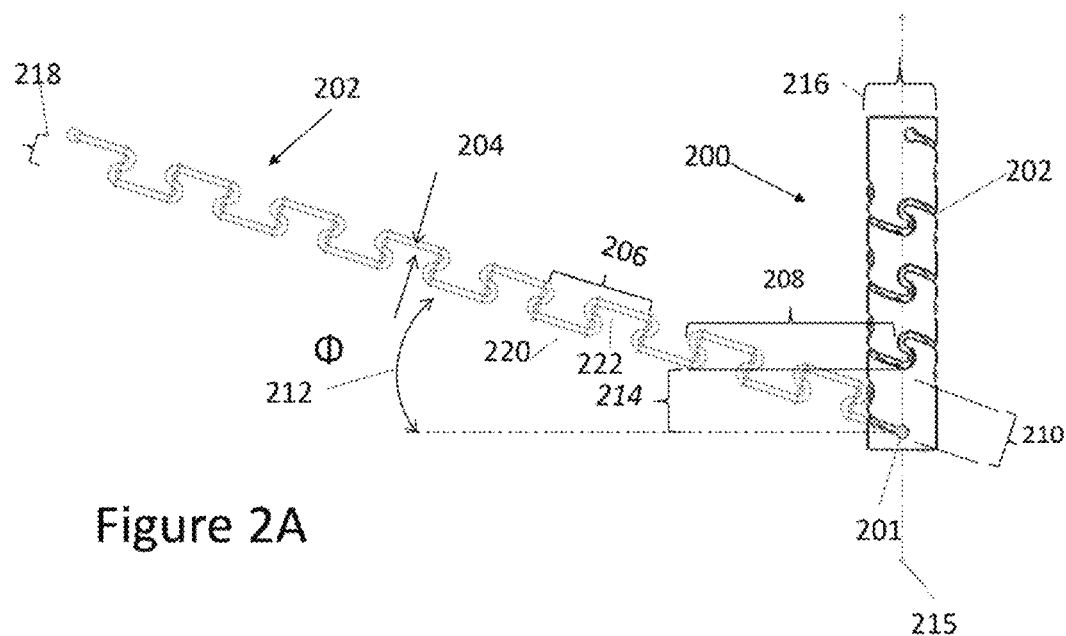
FIG. 2A illustrates the nomenclature used for the description of the sinuous helical slot, in an unwrapped condition of a flexible shaft segment.
Figure 2B:
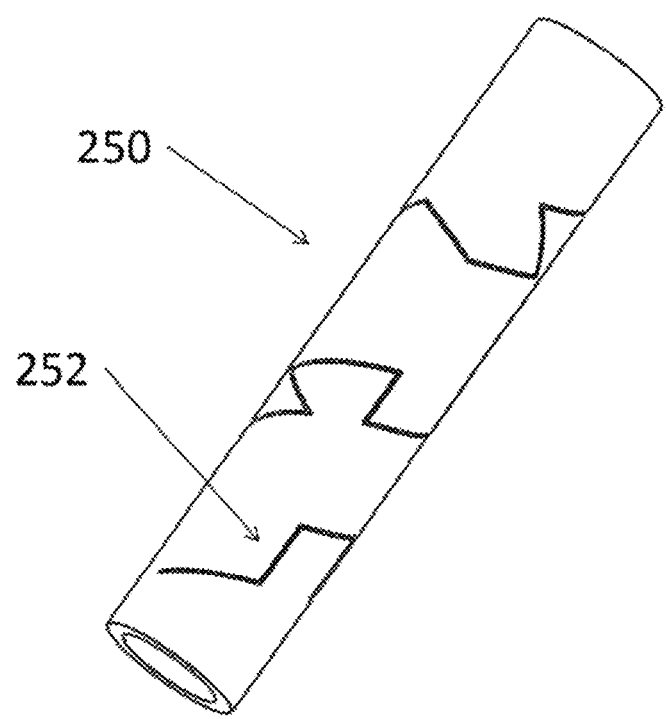
FIG. 2B illustrates a helical slot 252 on the shaft 250 has a straight configuration or combination of straight and curved portions that are in a random or repetitive pattern.

To better illustrate and define the characteristics of the invention, FIG. 2A illustrates a representative section of a shaft 200 containing a slot 202 following a sinuous path about a helical path along the longitudinal surface of the shaft. For Illustrative purposes, the sinuous path of the slot 202 is "unwrapped" from the shaft 200 to show the properties of the slot 202 and corresponding relationships.

Figure 2C:
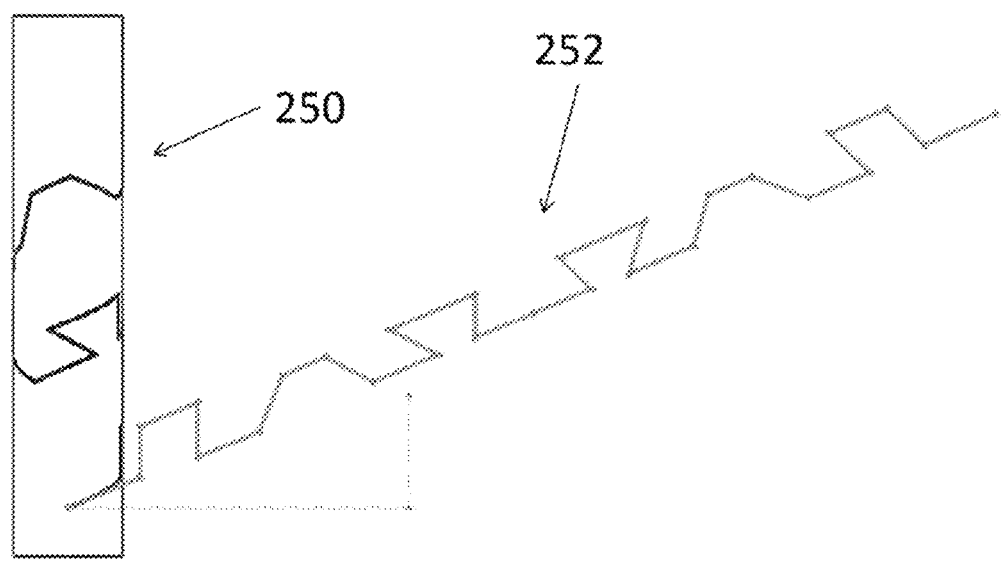
FIG. 2C illustrates the sinuous path of the slot 252 "unwrapped" from the shaft 250 to show the non-uniformity and repetitiveness of the slot configuration.

In the example illustrated in FIG. 2A a shaft 200 has a diameter 216 and a longitudinal axis 215. The slot 202 is formed from a number of cycles 206, each having a proximal dovetail tooth 220 and a distal dovetail tooth 222. The length of the cycles 206 contribute to the degree of flexibility and can vary over the length of the slot 202. The number of cycles 206 will also be determined by the circumference 208 of the shaft 200 into which is cut helical slot 202. The helix rise 210, or distance between proximal end 201 and subsequent cycles 206 of the slot 202, is determined based on desired flexibility. Other contributing factors to the degree of flexibility are the amplitude 218, or the height of the proximal tooth 220 and distal tooth 222 and the slot width 204. The helix angle 212 and the pitch 214 are further contributors to flexibility. Although the cycles ascending the slot are aligned in this and other figures, alignment is not a critical feature and the cycles can, and will with pattern changes, be unaligned In another embodiment of the invention illustrated in FIG. 2B a helical slot 252 on the shaft 250 has a straight configuration or combination of straight and curved portions that are in a random or repetitive pattern. FIG. 2C illustrates the sinuous path of the slot 252 "unwrapped" from the shaft 250 to show the non-uniformity and non-repetitiveness of the slot configuration.

It should be noted that when a shaft has more than one segment, or more than one slot per segment, the slot width, helix angle, pitch, cycle length and amplitude can all vary from slot to slot, segment to segment or within a single slot. This is applicable for all embodiment herein.

FIG. 3 is an illustration depicting the "Right Hand Rule" to define the rotation about an axis. For definition of the helical path, the "Right Hand Rule" for rotations is used to define the rotation about the shaft, FIG. 3. The direction of rotation is determined if the right hand grasps axis 101 of the shaft with the thumb 102 oriented in the direction of the shaft, fingers 103 will then curl in direction of positive rotation 105 for that axis which would correspond to a counter clockwise rotation about the axis if looking directly down at the tip of the thumb. If the right hand's direction is reversed about the shaft, i.e. the thumb pointed down in FIG. 3, a finger curl will be in the opposite or clockwise rotation.

Figure 4:
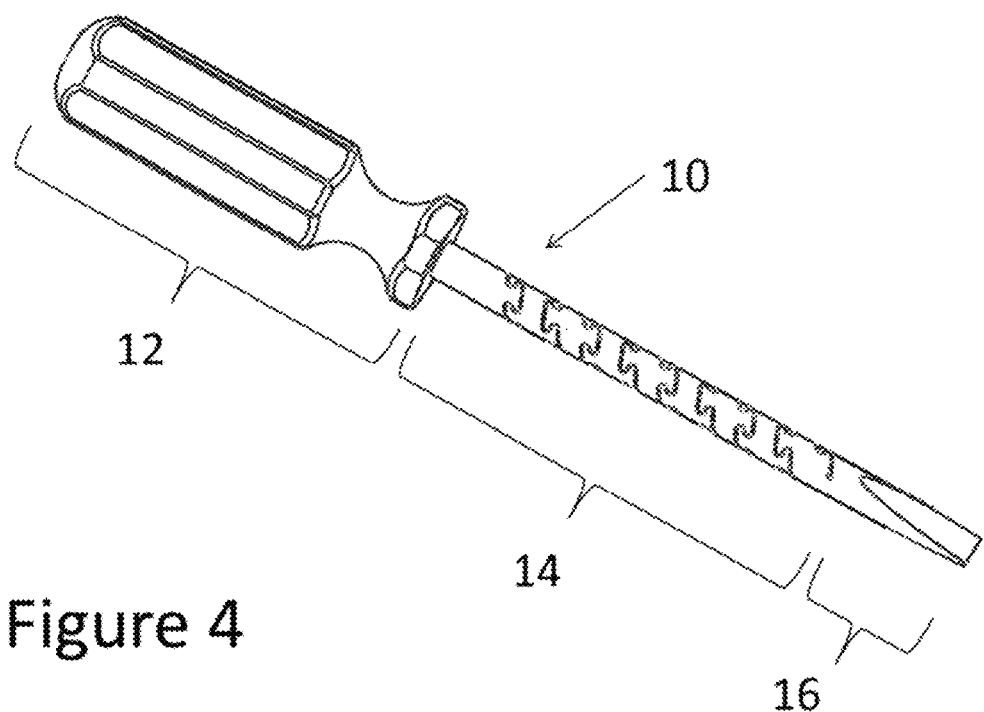
FIG. 4 shows a flexible screw driver 10 in accordance with the invention having a handle 12, a central flexible shaft 14 and a tip 16 that the user inserts into the screw head.
Figure 5:
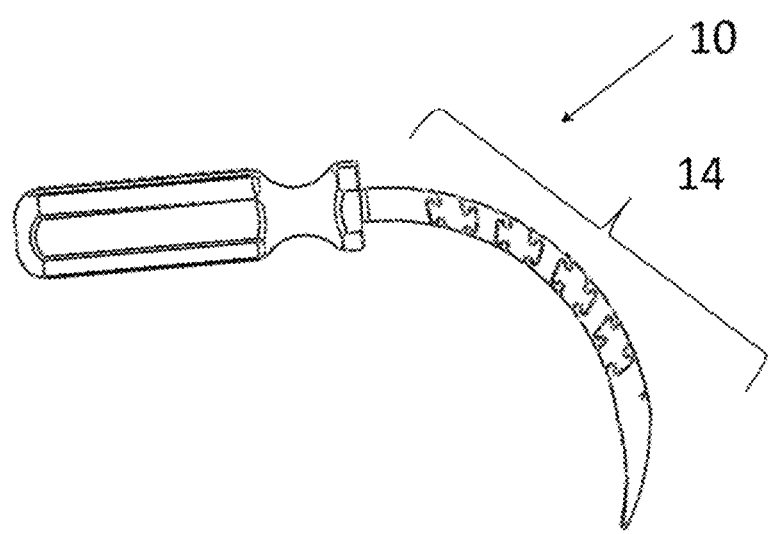
FIG. 5 shows a flexible screw driver 10 in accordance with the invention with the central flexible shaft 14 in a flexed position.

FIG. 4 illustrates the described invention when applied to a flexible screwdriver 10 having a flexible shaft 14 superimposed between a handle 12 and screwdriver tip 16. In FIG. 5 the screwdriver 10 has been bent to a flexed configuration, enabling the tip 16 to reach normally inaccessible screw heads. As the handle 12 is rotated the force is transferred, as with a standard screwdriver, to the tip 16. As the rotation occurs, the interlocking teeth release slightly and relock to maintain the curve while transferring the rotation. The more play between the teeth, achieved through the use of a wider slot, will increase the flexibility. Too wide of a slot however will compromise the shaft's integrity as well as reducing the rotation ratio between the handle 12 and the tip 16.

Figure 6:
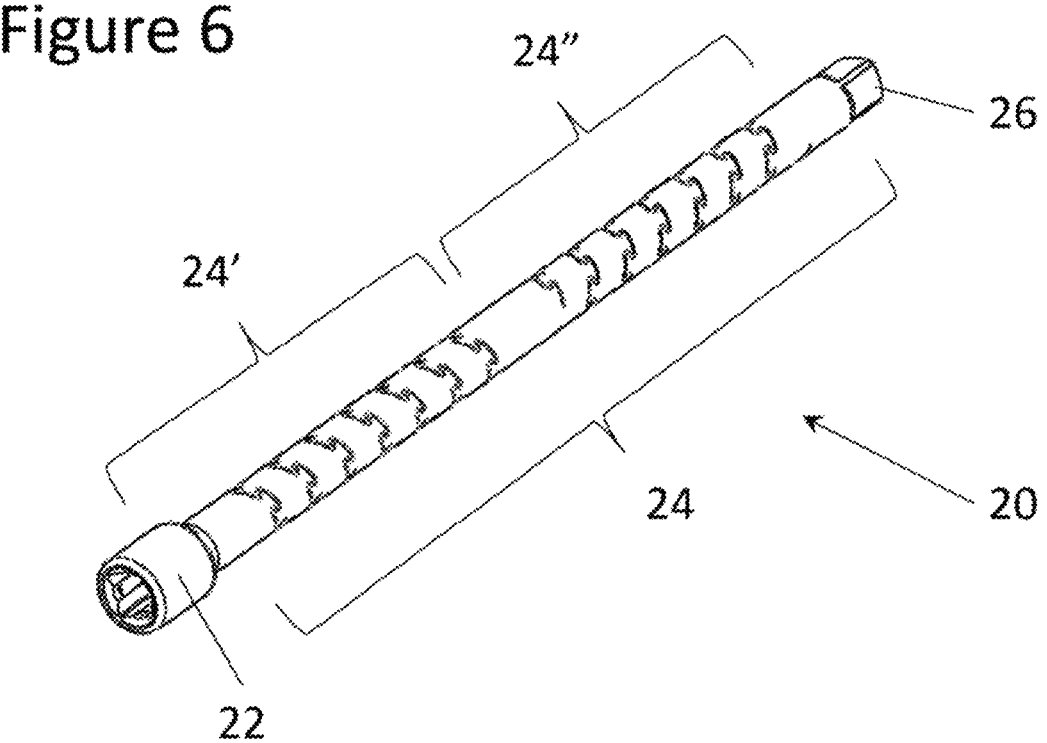
FIG. 6 shows a flexible socket extension 20 in accordance with the invention having a drive end 22, a central flexible shaft 24 composed of one or more flexible segments 24' and 24" and a socket drive tip 26 that the user inserts into a socket head to drive a bolt or other device.

FIG. 6 illustrates a flexible extension device 20 for a socket wrench in accordance with the invention having a drive end 22, a central flexible shaft 24 composed of, in this Figure, flexible segments 24' ascending in a clockwise direction and 24" ascending in an counterclockwise direction and a socket drive tip 26. This is for illustration and one or more than two can also be used and will be dependent on the end use and length and will be known to those skilled in the art. Although the extension for a socket wrench is illustrated, this is an example only and the drive end 22 and socket drive tip 26 can be changed to fit the applicable tool.

Figure 7:
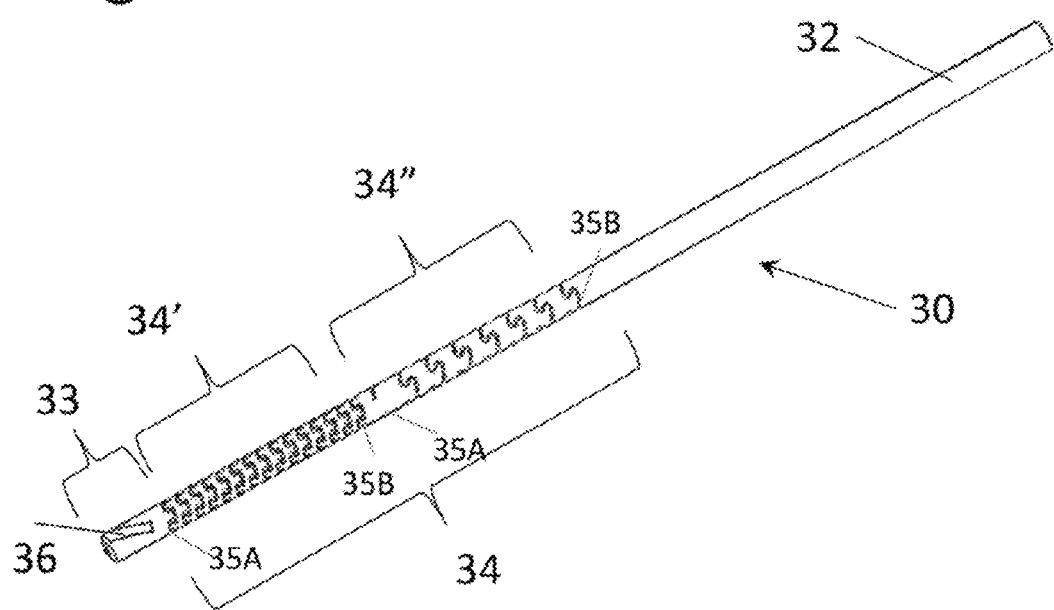
FIG. 7 shows a flexible reamer 30 in accordance with the invention having a drive end 32, a central flexible shaft 34 composed of one or more flexible segments 34' and 34" and a reamer tip 36 that the user inserts the cavity to be reamed.

FIG. 7 shows a tool for use as a flexible reamer 30 in accordance with the invention having a drive end 32, a central flexible shaft 34 composed of two flexible segments, clockwise distal segment 34' and counterclockwise proximal segment 34" and a reamer tip 33 with cutting flukes 36 for removing material in the object being reamed. Generally the outer diameter of the reamer is in the order of 1 to 25 mm.

Figure 8:
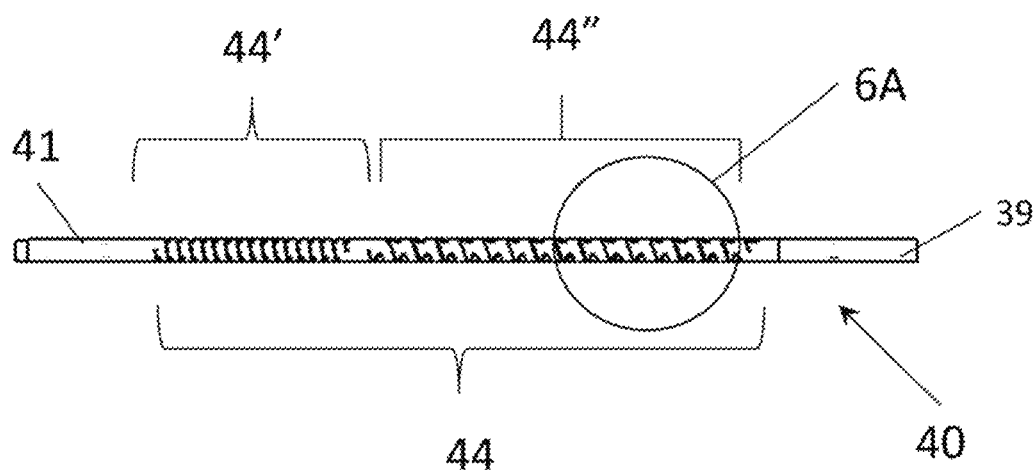
FIG. 8 shows an example of a flexible shaft configuration that can be used with any of the disclosed embodiments.
Figure 9:
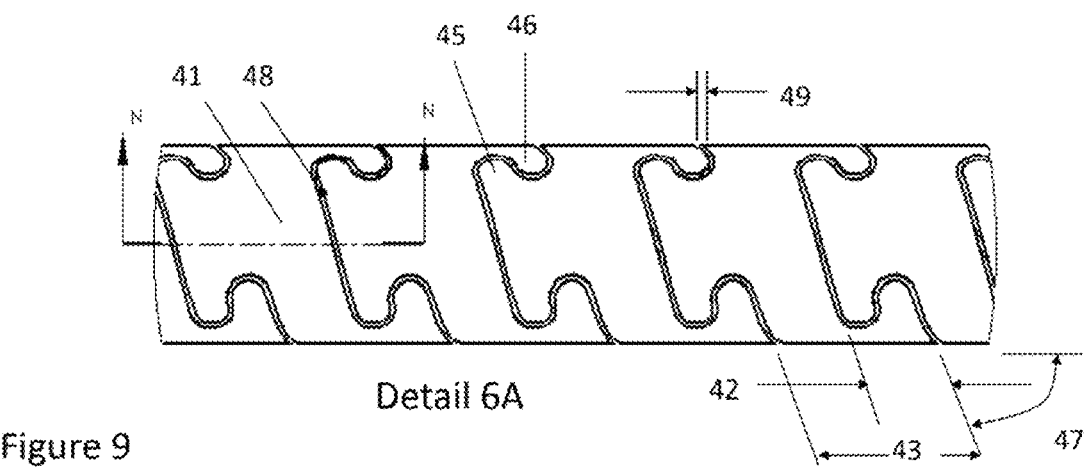
FIG. 9 is a detailed view of the serpentine slot comprising the flexible segment shown in 6A FIG. 8.

FIG. 8 is a diagrammatic illustration of a generalized flexible shaft 40 which has a leading end segment 41, flexible section 44 divided into two flexible segments, distal segment 44' and proximal segment 44" and a trailing segment 39. The exploded area of FIG. 9 is indicated in FIG. 8 by 6A. In this embodiment the leading end segment 41 is a threaded ended segment but other means, as known in the art, of securing the leading end segment 41 to the receiving material, such as bone, can be employed. In this embodiment flexible section 44' and flexible section 44" have different helical patterns, however this is for example only as is the length of each flexible section.

FIG. 9 is an exploded view of section 6A in FIG. 8 showing the serpentine slot 48 of the flexible section 44" of shaft 40. The slot 48, having a slot gap width 49, is cut with a general helix angle 47 of about 10 to 80 degrees with respect to the longitudinal axis of the section 44". The slot 48 is cut in a serpentine pattern having an amplitude 42 and interlocking teeth 46, 45 with a pitch 43. Typically the ratio of the amplitude 42 to the spacing 43 is between 0.1 and 0.8. For a higher angled slot helix, the spacing amplitude can be lower.

Figure 10:
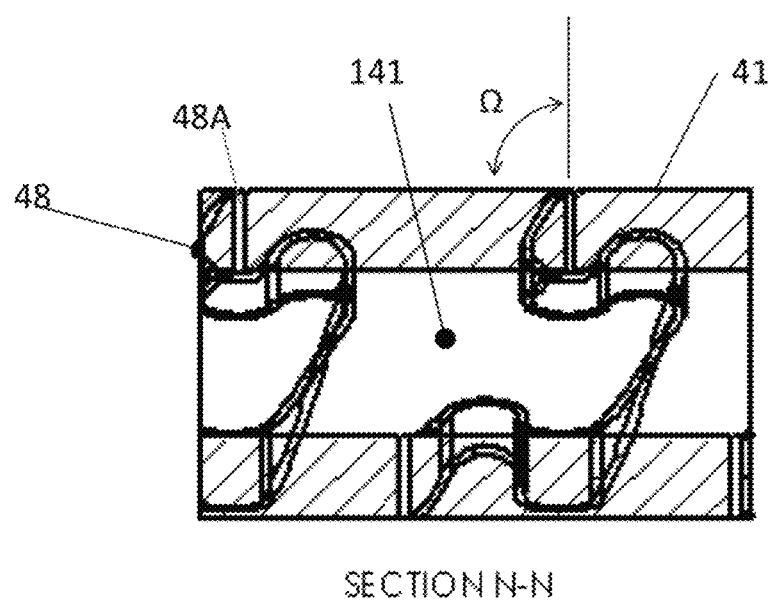
FIG. 10 is a sectional view of section N-N in FIG. 9.

FIG. 10 illustrates the section view N-N of FIG. 9. The slot 48 is representative of all the slots disclosed herein in the way that it is cut through the shaft 40 into the interior cavity 141 with the depth 48A of the slot 48 being equal to the thickness of the shaft 40. Although the slots disclosed herein are of different patterns, this is purely a function of flexibility and all have the same basic construction. In the following description of the criteria of the slots, no reference numbers specific to other figures are used, as the criteria are applicable to all slot configurations. Advantageously, the slot is cut perpendicular to a plane tangent to the outer surface of the shaft as shown in FIG. 10. Alternatively, the slot can be cut at some slot angle Ω to the longitudinal axis of the shaft and/or the plane tangent to the outer surface, as shown in FIG. 10. The angle can be in the range from zero (perpendicular) to about 75 degrees thereby forming an undercut. Preferably the angle if not perpendicular, is in the range from about 30 to 45 degrees from the perpendicular. The undercut can be formed by cutting offset from the radius, or offsetting from a plane tangential to the surface of the shaft at the slot.

A variety of slot patterns are illustrated in U.S. Pat. Nos. 6,053,922 and 6,447,518, the disclosure of which is incorporated herein by reference, as though recited in detail.

Figure 11:
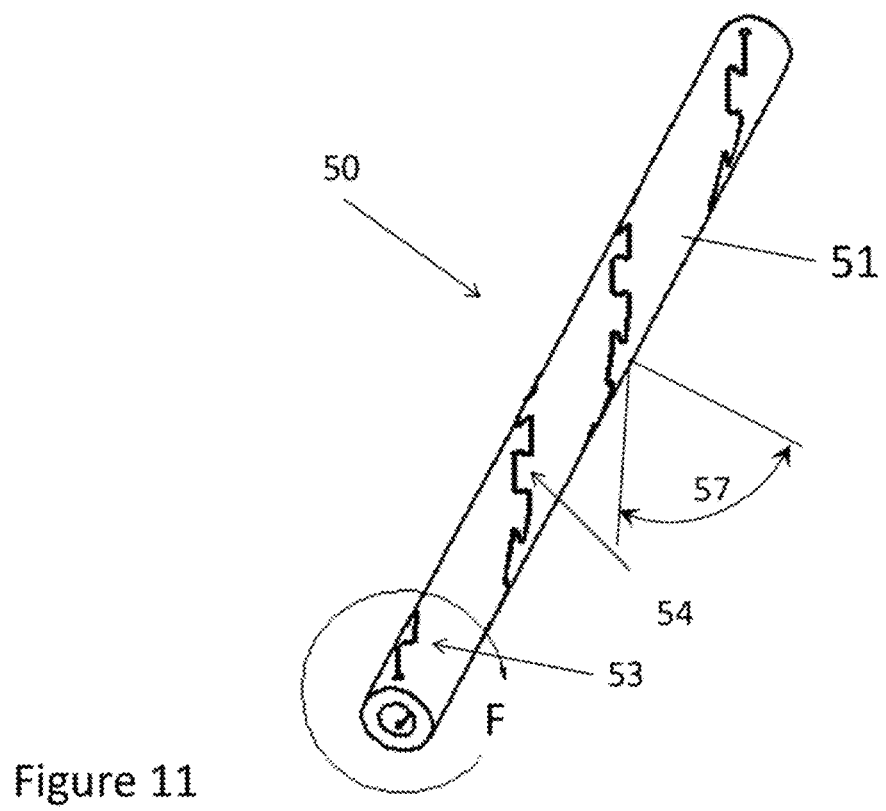
FIG. 11 shows flexible shaft 50 with a sinuous helical slot at a high angle relative to the shaft in accordance with the invention.
Figure 12:
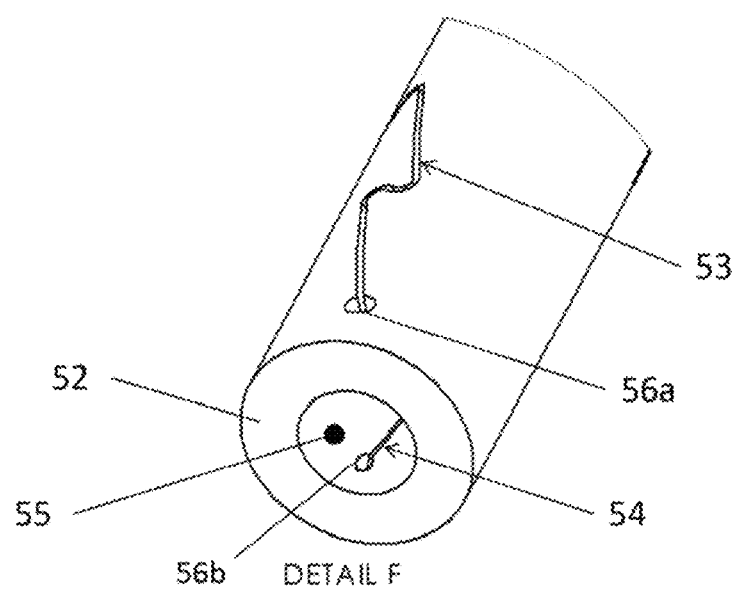
FIG. 12 is a detail view of Detail F in FIG. 11.
Figure 13:
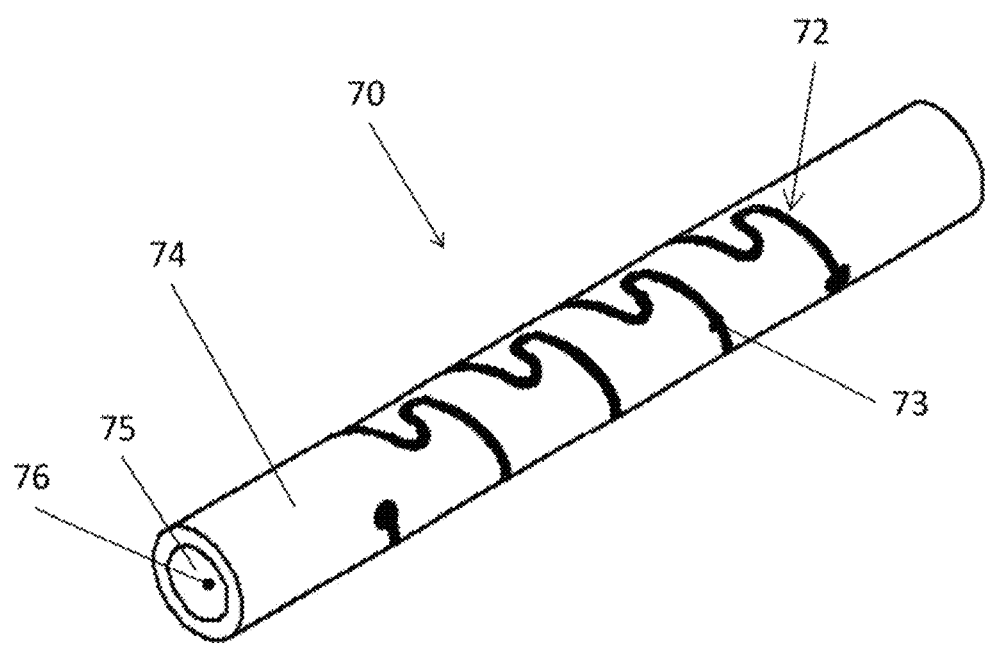
FIG. 13 is a schematic representation of a segment of flexible shaft 70, showing a general pattern of the sinuous, serpentine slots along the length of the rod with an elastomeric material filling the slot in accordance with the invention.

The flexible element 50, as illustrated in FIGS. 11 and 12, consists of a hollow tube 58 having wall 52 with an outer surface 51 and a hollow central core 55 with two slots 53 and 54. In this instance the slots 53, 54 are cut into the wall 52 at a very high helix angle 57 relative to a line normal to the longitudinal axis of the shaft 50. Detail F of FIG. 12 shows the start of the slots 53 and 54 having circular ends 56a and 56b respectively, to reduce the stress concentration at the end of the slot. The use of the circular ends 56a and 56b at the beginning and end of all slots reduces the stress at the end of the slot and substantially reduces the risk of the shaft cracking or breaking under pressure. Although in some uses the pressure applied will not be sufficient to break the shaft, in many industrial uses the pressure applied can cause damage.

In order to provide the desired flexibility, while maintaining support, the width of the slot will be dependent upon the desired flexibility, dimensions of the shaft and the helix angle. Generally, a rod having a diameter in the range from about 0.04 to about 4.0 inches when the helix angle is less than 45 degrees, the slot width should not exceed of about 0.005 to about 0.20 inches. Or alternatively stated, the slot width is between about 2.5% and about 20% of the diameter of the element. The slot width typically determines the flexibility of the element; a larger slot width produces a more flexible element than an element with a smaller slot width. The ratios between slot design and shaft diameter to achieve optimum flexibility and torque are dependent upon end use. Using the teachings set forth herein, a person skilled in the art can determine the optimal slot design to diameter based on the end application.

The disclosed turning tool can be used in a number of applications, including medical, and in some applications, there is significant disadvantage of having open slots in that debris and foreign material can get into the slot and impede the performance of the shaft. To overcome these deficiencies, the slot can be filled with a resilient flexible or elastomeric material. The degree of filling can vary from just the slots being filled to the entire central cavity and exterior of the shaft being filled. Representative variations, although not exhaustive, in the amount of filling is illustrated in the following figures. It should be noted that the type of elastomeric material used can also be varied in its material properties, thereby further controlling the amount of flexibility.

The embodiment illustrated in FIGS. 13 through 16 shows a resilient flexible or elastomeric material 73 filling only within the slot 72 of the element 70. The exterior surface 74 of the element 70, as well as the hollow interior cavity 76, remains uncovered by the elastomeric material 73 as does the interior surface 75. The addition of the elastomeric material 73 to the slot 72 provides resistance to the flexibility of the element 70 as well as preventing debris or foreign material from entering the slot. It should also be noted that the elastomeric material does not necessarily have to fill all slots in the element, with the placement of filled and unfilled slots affecting the flexibility. FIG. 14 shows a longitudinal view of shaft 70 and FIGS. 15 and 16 show the sections A-A and B-B of the shaft 70, respectively. FIGS. 15 and 16 show the elastomeric material filling 73 only within the slot 72 in both a cutaway side view and an end view.

It should be noted that in addition to prevent debris from entering the slot, the elastomeric material reduce the flexibility and provide some structural integrity to the shaft, permitting wider slots to be used in some applications. The degree of added integrity is dependent upon the application of the elastomeric material as well as the elasticity of the material.

The embodiment illustrated in FIGS. 17, 18 and 19, has a resilient flexible or elastomeric material 83 filling the slot 82 as well as covering both the interior surface 85 and exterior 84 surfaces of the element 80. FIGS. 18 and 19 show the sections A-A and B-B of the shaft 80 of FIG. 17, respectively. FIG. 18 illustrates the interior surface 85 of the element 80 coated along with the coated exterior 84 and filled slots 82. FIG. 19 illustrates the elastomeric material 83 completely filling the slot 82 and coating the interior and exterior surfaces.

In another variation, only the exterior surface or the interior surface of the shaft remains uncovered by the material, with the opposing surface being covered. The combinations taught herein are for example only and any combination of elastomeric material covering and/or filling with any design, helical angle, slot angle or number of slots can be used to vary the flexibility.

Figure 20:
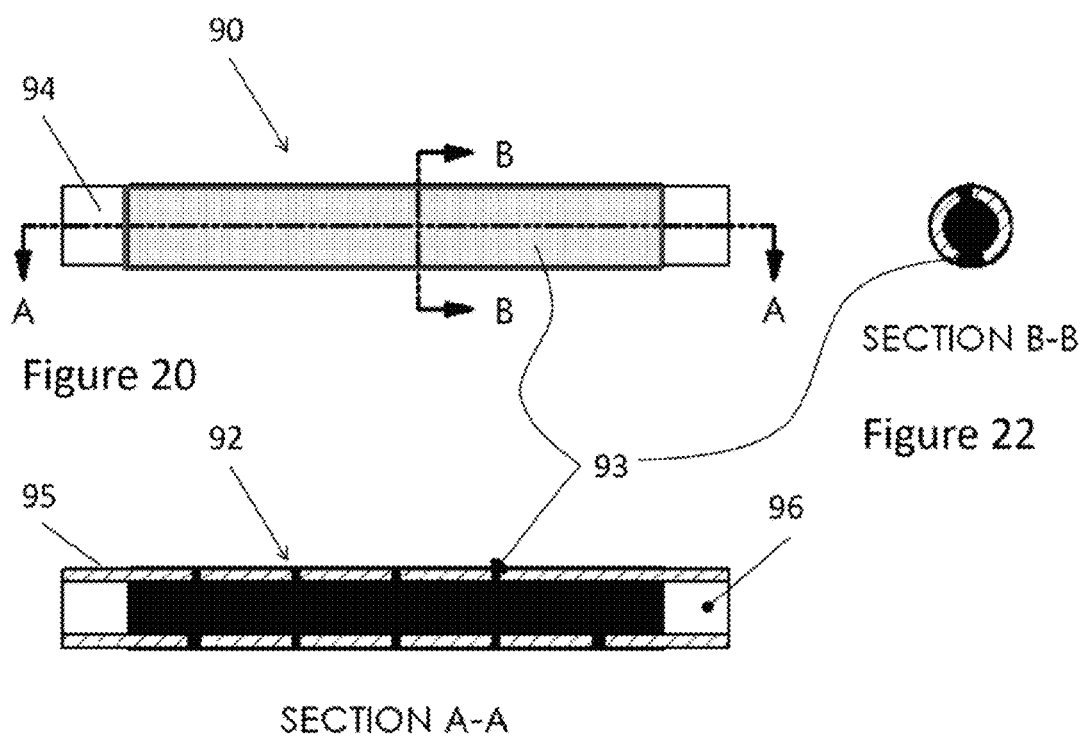
FIG. 20 is an illustration the flexible shaft 90 with a resilient filler covering the flexible region of shaft 90, filling the slot and filling the interior cavity in accordance with the invention.

The embodiment illustrated in FIGS. 20, 21 and 22, shows a resilient flexible or elastomeric material 93 filling the central hollow interior cavity 96 of shaft 90, the slot 92 and the exterior surfaces 94 of the element 90. This embodiment provides the greatest resistance to flexing when using the hollow shaft and elastomeric filling of the central interior cavity 96. Although only the portion of the shaft 90 having a slot 92 is shown filled with the elastomeric material 93, the unslotted portions of the hollow interior cavity 96 can also be filled.

In another embodiment, the flexible shaft has multiple serpentine, sinuous slots about the shaft either in a clockwise and/or counter-clockwise rotation in a helical fashion. Cutting a single helical slot into a tube yields what is referred to as a single-slot shaft. Similarly, a double-helix shaft can be constructed provided that the helix angle is the same, and a second slot is cut in the space between the slots of the first. For certain applications, triple and quadruple slots are in use. In another aspect of the invention, one or more sections of shaft, have both the serpentine helical slot spiral in one direction and a second section, or multiple sections, rotated in the opposite direction. Another aspect of the invention is to have a double helix with one or more helix rotated in a clockwise direction, and a second or more helixes in a counter-clockwise rotation within the same section of shaft. With the combination of clockwise and counter clockwise rotations, the elongation or contraction can be minimized.

Figure 23:
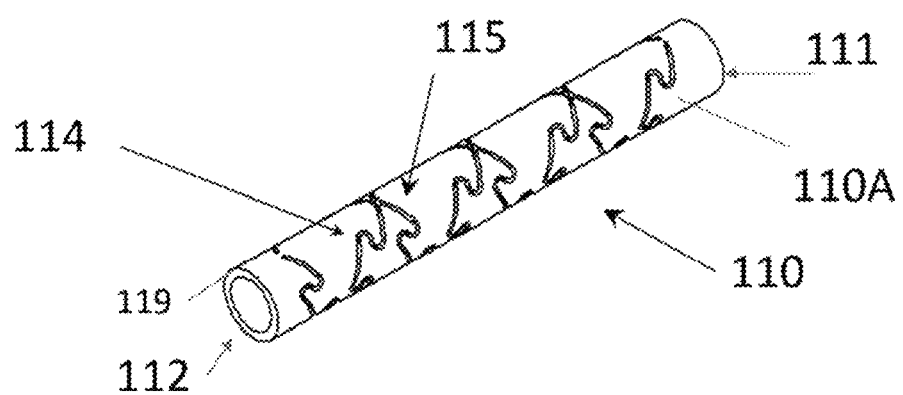
FIG. 23 is an illustration of an intersecting, double helix pattern with a clockwise and counter-clockwise sinuous helical slot in accordance with the invention.

FIG. 23 illustrates a shaft 110 with a near or proximal end 112 and a far or distal end 111, having a counter-clockwise sinuous helical slot 114 and an intersecting clockwise sinuous helical slot 115 cut into the wall 119.

Figure 24:
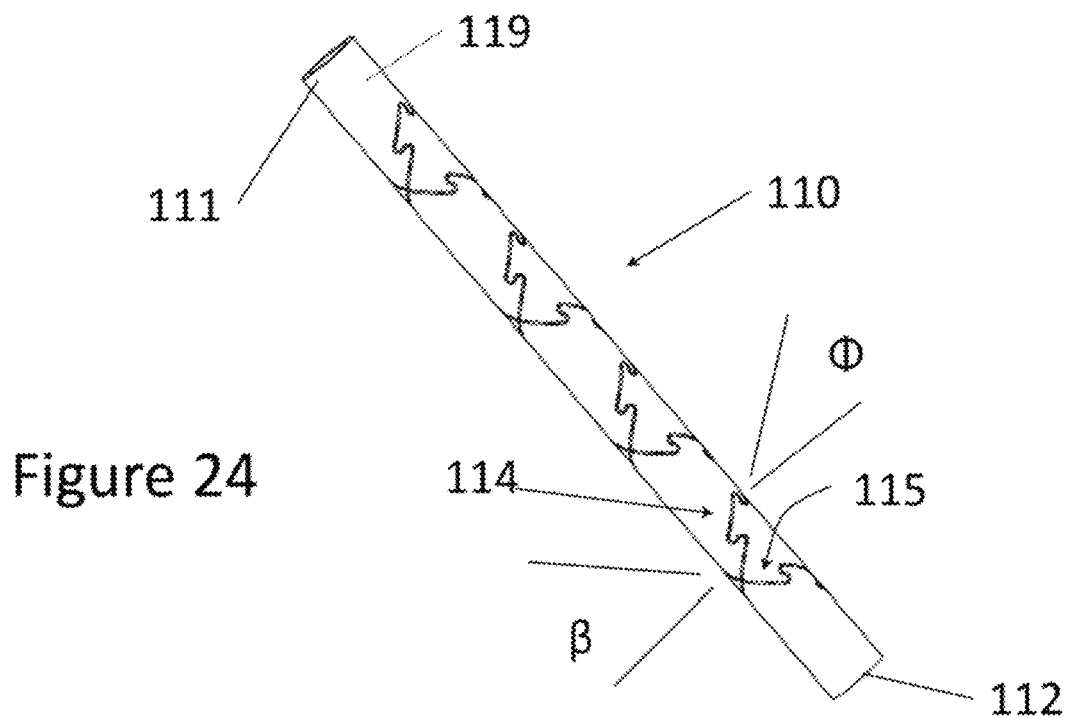
FIG. 24 is an isometric view of FIG. 23.

FIG. 24 illustrates the helical angle of the counterclockwise helical slot 114 and clockwise helical slot 115 as φ and β, respectively, starting at the near or proximal end 112 and extending to the far or distal end 111. The helical angle of the slots 114 and 115 can range from about 30 degrees to about 85 degrees the ratio of the amplitude of sinuous path to the pitch of the slot is in the range from greater than about 0.1 to about 0.8. The helical angles φ and β, preferably being from 45 to 75 degrees, can be equal or different as the degree of desired flexibility will dictate the respective angles.

FIG. 25 is a horizontal view of the shaft 110 with intersecting slots 114 and 115 extending through the wall 119 into the internal cavity 123 and indicating the detailed area B illustrated in FIG. 26.

FIG. 27, is a close up of detail C in FIG. 26 showing the interlocking teeth 117 and 118 created by the slot 114 with a gap 116 and is representative of all slots.

Figure 28:
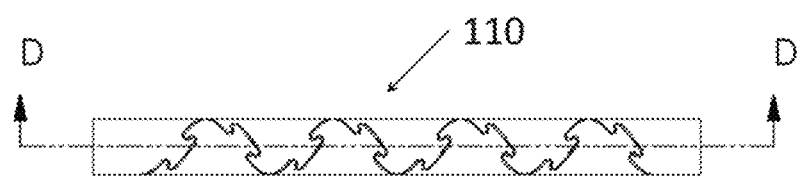
FIG. 28 is the horizontal view of the double helix pattern flexible shaft in FIG. 23 showing the orientation for Section D-D.
Figure 29:
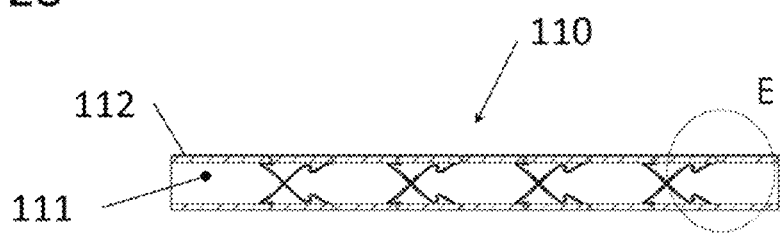
FIG. 29 is a sectional illustration though the longitudinal axis D-D of the central segment in FIG. 28.

FIG. 28 a horizontal view of shaft 110 showing the location of Section D-D about the central axis of shaft 110. The sectional view D-D of shaft 110 in FIG. 29 illustrates the interior cavity of the shaft 123 and the location of the detailed area E.

Figure 30:
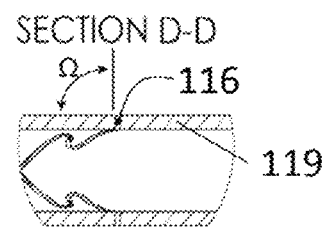
FIG. 30 is a magnified view of the area E in FIG. 29 in accordance with the invention.

FIG. 30 is the detail view of Detail E illustrating the slot angle Ω of the slot gap 116 cut through the wall 119 relative to the longitudinal surface of the shaft 110. The slot angle would generally be in the range of 0 degrees to 45 degrees (±45 degrees from the normal).

Figure 31:
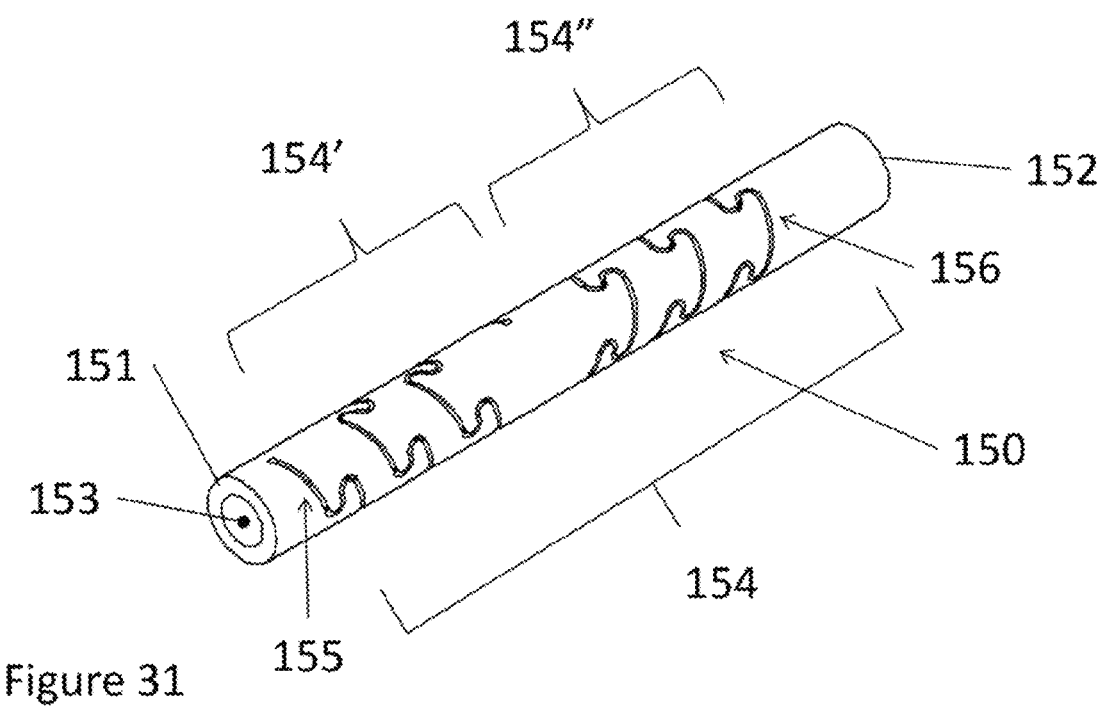
FIG. 31 is an illustration of a multiple helix pattern with a clockwise flexible segment and a counter-clockwise flexible segment in accordance with the invention.

In another embodiment of the invention, as illustrated in FIG. 31, the double segment, opposite helix flexible shaft 150 with an internal cavity 153, near end 151, far end 152 and a flexible segment 154 which contains two or more areas of flexibility 154' and 154" having sinuous helical slots 155 and 156, respectively. The rotation of the slots are such that the general helical rotation of one flexible area is generally in the counter-clockwise orientation while another slot orientation is in the clockwise rotation.

Figures 32, 33:
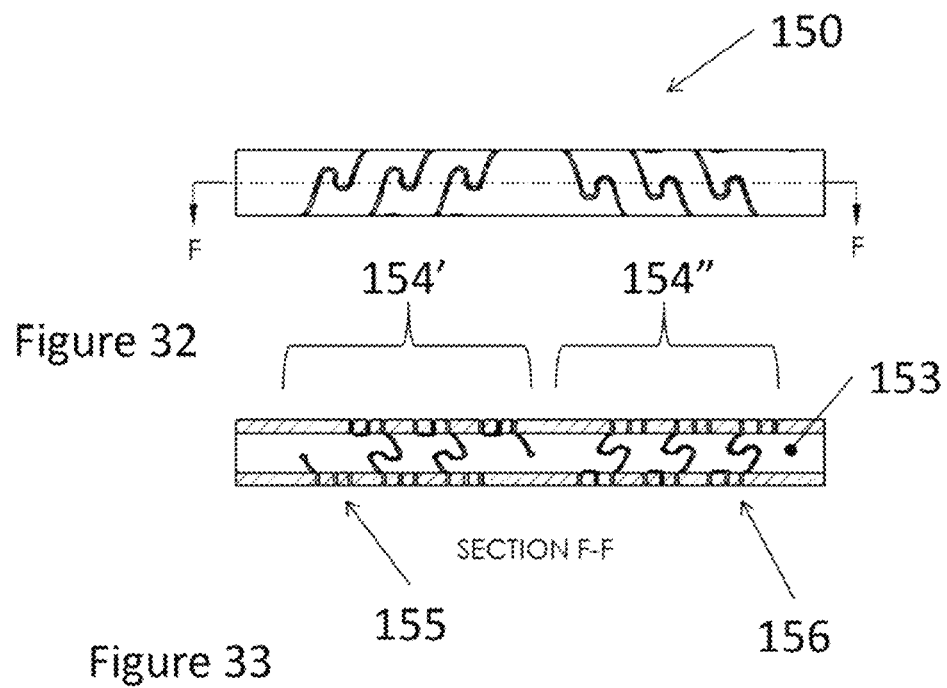
FIG. 32 is the horizontal view of the multiple helix pattern flexible shaft in FIG. 31 showing the orientation for Section F-F.
FIG. 33 is a sectional illustration though the longitudinal axis F-F in FIG. 32.

FIG. 32 shows a horizontal view of the shaft 150 illustrated in FIG. 30 and the location of section F-F for illustration in FIG. 33.

Figure 34:
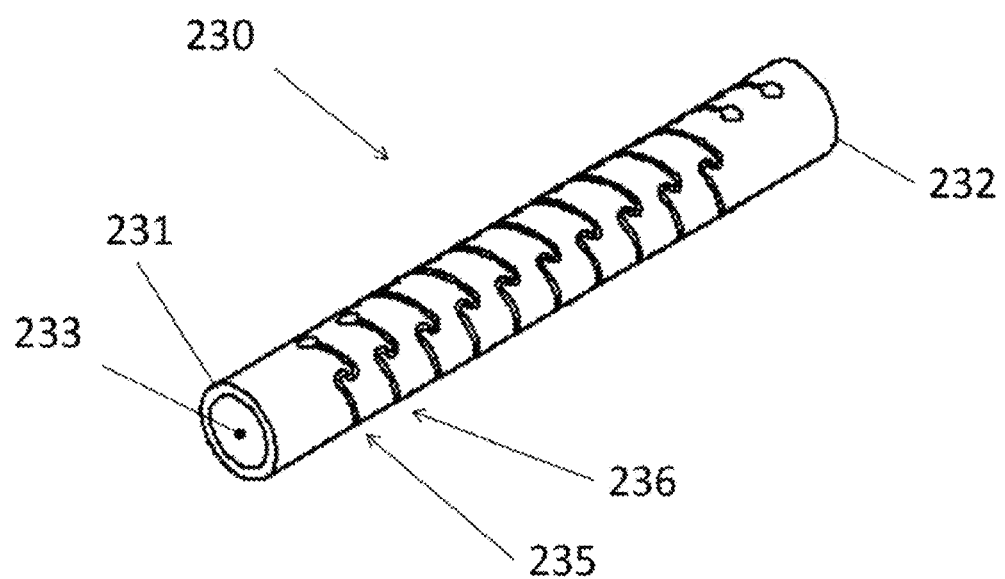
FIG. 34 is an illustration of a multiple helix pattern, flexible segment in accordance with the invention.

FIG. 34 illustrates an additional embodiment of the invention whereby there are two or more serpentine, sinuous helical slots in the shaft 230 with an internal cavity 233, proximal end 231, distal end 232 and a the flexible segment between the two ends which contains two or more sinuous helical slots 235 and 236, preferably in the same rotational direction. The characteristics described previously with regard to slot pattern design, number of slot pattern cycles per revolutions, slot amplitude, slot width, slot undercut and shaft filler or encapsulation can be the same for both, or multiple slots or they can be different to change the flexibility characteristics of the device.

Figure 35:
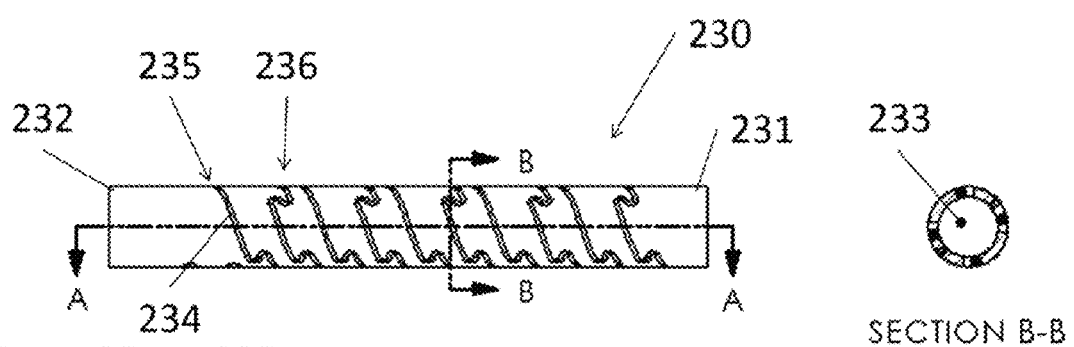
FIG. 35 is the sectional view A-A of the multiple helix pattern flexible shaft in FIG. 34 in accordance with the invention.

FIG. 35 illustrates the horizontal projection of the shaft 230 and the location of Sections A-A and B-B. In this embodiment there is a difference in the slot configuration for slot 235 as opposed to 236. Slot 235 has an extended non-sinuous helical portion 234 compared to slot 236. The sinuous pattern for any of the slots may be a repeating pattern or could be a random pattern about the helical path and they do not necessarily have to be the same for any or all slots.

FIG. 36 illustrates the cross section B-B of the shaft 230 to show the open internal cavity 233 that could be filled with a polymer or other flexible material. As previously described the embodiment of the flexible section or sections have a flexible segment that has at least one helical, sinuous slot within a section of the element that is embedded within a polymer or other flexible material so as to fill the slot with the flexible material.

Figure 37:
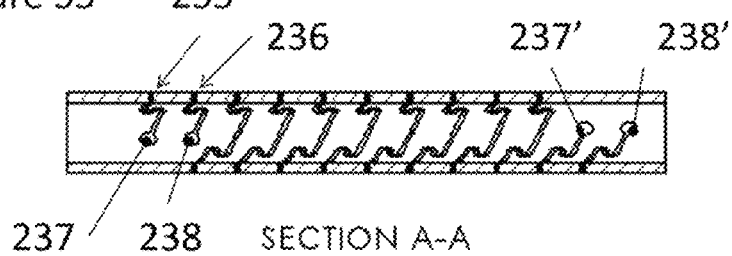
FIG. 37 is the longitudinal cross section A-A in FIG. 35 in accordance with the invention.

As noted heretofore, in order to reduce the stress concentration effect at the ends of the sinuous slots, larger diameter holes are placed at the ends of the slots. Illustrated in FIG. 37 are near first slot hole 237 and far first slot hole 237' drilled at the end of slot 235 and far second slot hole 238 and near second slot hole 238' drilled at the ends of slot 236.

Figure 38:
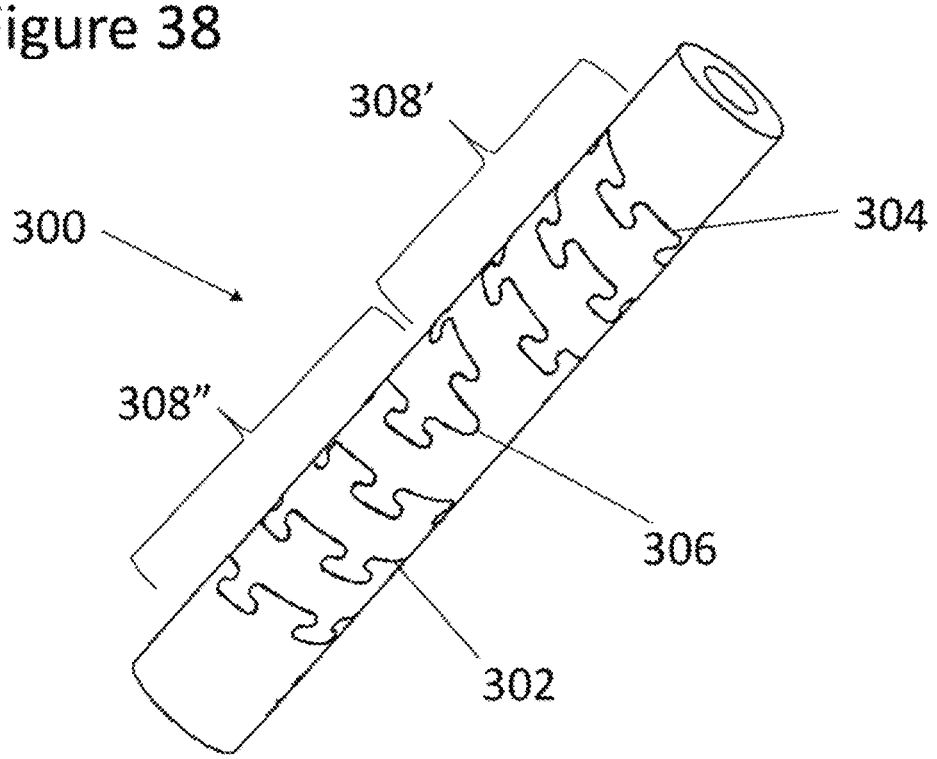
FIG. 38 illustrates the shaft having two contiguous slots reversing direction without a rigid divider in accordance with the invention.

In FIG. 38 the shaft 300 has proximal slot 302 and distal slot 304 cut contiguously, changing directions at the turning point 306. Thus the two segments 308' and 308" are adjacent to, and contiguous with, one another. The change in direction without a rigid portion between the segments can, depending on shaft thickness, slot width, etc., weaken the integrity of the shaft 300. However, in applications where the contiguous nature of the segments is advantageous, those skilled in the art can, in conjunction with the teachings herein, determine the appropriate ratios.

Figure 39:
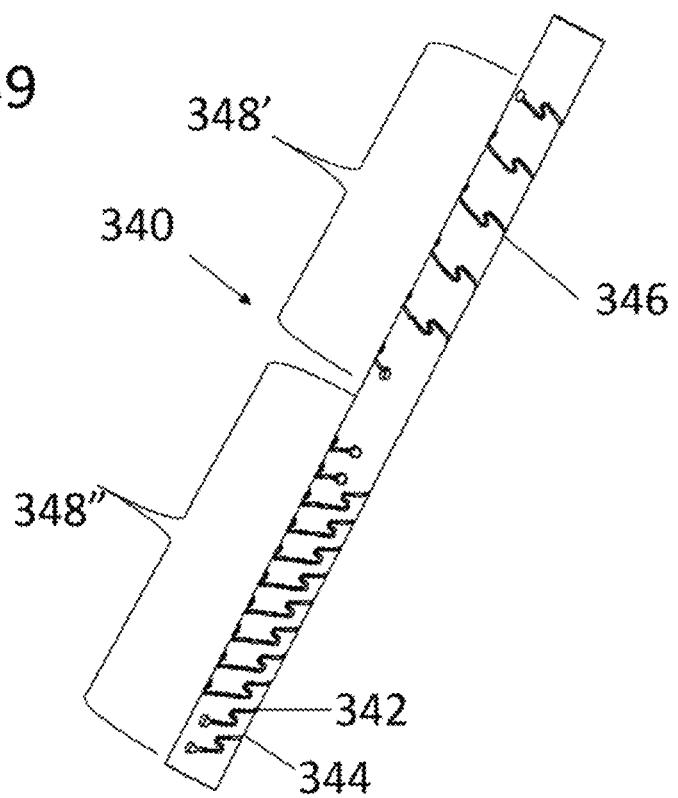
FIG. 39 illustrates a shaft having a double, parallel slot in one segment and a single slot in a second segment, in accordance with the invention.
Figure 40:
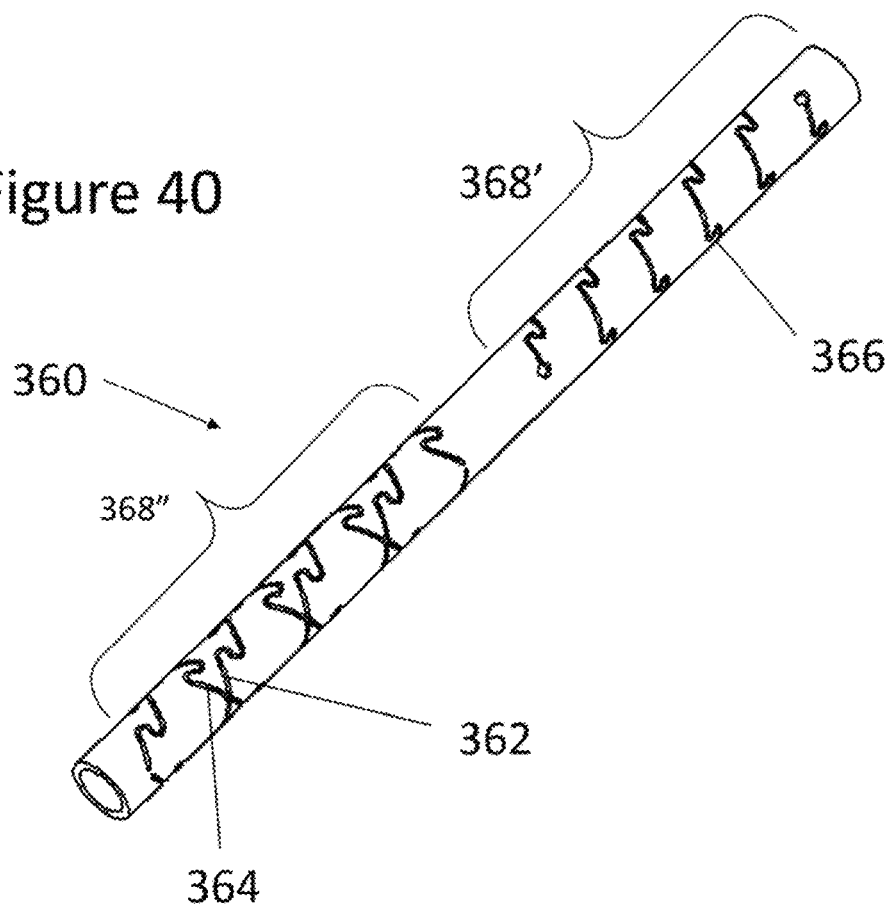
FIG. 40 illustrates a shaft having a double slot, each slot ascending in an opposite direction, and a single slot in a second segment, in accordance with the invention.

In FIG. 39 the shaft 340 is illustrated with parallel first proximal slot 342 and second proximal slot 344 in a first segment 348 and a single slot 346 in distal segment 348'. Another combination of slots is illustrated in FIG. 40 wherein the proximal segment 368" has a sinuous slot 264 ascending in a first direction and sinuous slot 362 ascending in a second direction while the second segment 368' has a single sinuous slot 366.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A flexible shaft for a tool, said flexible shaft being a rigid material and comprising:
    a. a rigid first end, said rigid first end being capable of receiving an instrument to impart rotary motion,
    b. a rigid second end, said rigid second end being dimensioned to receive a tool to receive said rotary motion and transmit said rotary motion to a tool,
    c. a body between said rigid first end and said rigid second end, said body having:
        an outer surface,
        an inner cavity having a surface,
        a longitudinal surface,
        at least one segment, each of said at least one segment having a segment proximal end and a segment distal end,
        at least one sinuous slot within at least one of said at least one segment, each of said at least one sinuous slot having:
            a width,
            a depth from said outer surface to said inner cavity,
            a start point, said start point having a circular end, said start point being a first predetermined distance from said rigid first end, and
            an end point, said end point having a circular end, said end point being a second predetermined distance from said rigid first end,
        said at least one sinuous slot being cut in a helical path along said longitudinal surface of said body to form interlocking teeth to enable flexibility within said at least one segment, a first of said at least one sinuous slot ascending a first of said at least one segment from said start point of said first of said at least one sinuous slot to said end point of said first of said at least one sinuous slot, in a first rotational direction,
        wherein said rotary motion is transferred by said interlocking teeth locking with adjacent teeth to transfer said rotary motion from said rigid first end to said rigid second end while said body is unbent or bent about an axis.

2. The flexible shaft of claim 1 wherein at least another of said at least one sinuous slot ascends another of said at least one segment in a helical path along said longitudinal surface from said start point of said another at least one sinuous slot to said end point of said another at least one sinuous slot, in said first rotational direction.

3. The flexible shaft of claim 1 wherein at least another of said at least one sinuous slot ascends another of said at least one segment in a helical path along said longitudinal surface from said start point of said another of said at least one sinuous slot to said end point of said another of said at least one sinuous slot, in a second rotational direction.

4. The flexible shaft of claim 1 wherein at least another of said at least one sinuous slot ascends said first of said at least one segment from said start point of said another of said at least one sinuous slot in a first rotational direction, said start point of said another of at least one sinuous slot being spaced from said start point of said first of said at least one sinuous slot, said first of said at least one sinuous slot and said another of said at least one sinuous slot crossing sinuous paths.

5. The flexible shaft of claim 4 wherein a first of said at least one sinuous slot ascends another of said at least one segment from said start point of said first of said at least one sinuous slot to said end point of said first of said at least one sinus slot in a first rotational direction, and a second of said at least one sinuous slot ascends from said start point of said second of said at least one sinuous slot in a second rotational direction, said start point of said second of said at least one sinuous slot being spaced from said start point of said first of said at least one sinuous slot, said first of said at least one sinuous slot and said second of said at least one sinuous slot crossing sinuous paths.

6. The flexible shaft of claim 1 wherein another of said at least one sinuous slot ascends said first of said at least one segment from said start point of said another of said at least one sinuous slot in said first direction, said start point of said another of said at least one sinuous slot being spaced from said start point of said first of said at least one sinus slot, said first of said at least one sinuous slot and another of said at least one sinuous slot having parallel spaced ascending paths.

7. The flexible shaft of claim 6 wherein a first of said at least one sinuous slot ascends another of said at least one segment from a start point of said first of said at least one sinuous slot in said first direction, and a second of said at least one sinuous slot ascends said another of said at least one segment from a start point of said second of said at least one sinuous slot spaced from said start point of said first of said at least one sinuous slot, said first of said at least one sinuous slot and said second of said at least one sinuous slot having parallel spaced ascending paths.

8. The flexible shaft of claim 1 wherein another of said at least one sinuous slot ascends a subsequent of said at least one segment in a helical path along said longitudinal surface of said body in a second rotational direction from said start point of said another of said at least one sinuous slot to said end point of said another of said at least one sinuous slot, in a second direction.

9. The flexible shaft of claim 1 wherein a first of said at least one sinuous slot ascends another of said at least one segment from said start point of said first of said at least one sinuous slot in a first direction, and another of said at least one sinuous slot ascends said another of said at least one segment from said start point of said another of said at least one sinuous slot spaced from said start point of said first of said at least one sinus slot in a second direction, said start point of said another of said at least one sinuous slot being spaced from said start point of said first of said at least one sinuous slot, a first of said at least one sinuous slot and said another of said at least one sinuous slot crossing sinuous paths.

10. The flexible shaft of claim 1 wherein said segment distal end of a first of said at least one segment is separated from said segment proximal end of a subsequent segment by a nonflexible segment.

11. The flexible shaft of claim 1 wherein said end point of said at least one sinuous slot within said segment distal end of a first of said at least one segment is contiguous with said start point of said at least one sinuous slot within segment proximal end of a subsequent segment.

12. The flexible shaft of claim 1 wherein each of said at least one sinuous slot has a helical angle of about 30 to 85 degrees from the longitudinal axis.

13. The flexible shaft of claim 1 wherein each of said at least one sinuous slot has a helical angle of about 45 to 75 degrees from the longitudinal axis.

14. The flexible shaft of claim 13 wherein said angle is in the range of about one to about 75 degrees.

15. The flexible shaft of claim 13 wherein said angle is in the range of about 30 to about 45 degrees.

16. The flexible shaft of claim 1 wherein at least one of said at least one sinuous slot has a helical angle different from the helical angle of another of said at least one sinuous slot.

17. The flexible shaft of claim 1 wherein at least one of said at least one sinuous slot has a depth perpendicular to a plane tangent to the outer surface of said body.

18. The flexible shaft of claim 1 wherein at least one of said at least one sinuous slot has a depth at an angle with a plane tangent to the outer surface to form an undercut.

19. The flexible shaft of claim 1 wherein at least one of said at least one sinuous slot has a width of about 0.005 to about 0.25 inches.

20. The flexible shaft of claim 1 wherein at least one of said at least one sinuous slot has a width of about 2.5% to about 20% of a diameter of said body.

21. The flexible shaft of claim 1 wherein said width of said sinuous slot contributes to the flexibility of said shaft.

22. The flexible shaft of claim 1 wherein said instrument is a handle.

23. The flexible shaft of claim 1 wherein said instrument is powered.

24. The flexible shaft of claim 1 wherein said tool is a screwdriver.

25. The flexible shaft of claim 1 wherein said tool is a reamer.

26. The flexible shaft of claim 1 wherein said tool is an extension bar.

27. The flexible shaft of claim 1 further comprising a elastomeric material, said elastomeric material applied to at least one from the group of interior cavity, sinuous slot, exterior surface, interior cavity, said surface of said interior cavity.

28. The flexible shaft of claim 1 wherein each of said at least one segment has a sinuous slot configuration from the group comprising single sinuous slot first rotational direction, single sinuous slot second rotational direction, multiple sinuous slots first rotational direction and multiple sinuous slots in a first rotational direction and a second rotational direction.

29. A flexible shaft for a tool, said flexible shaft being a rigid material and comprising:
  a. a rigid first end, said rigid first end being capable of receiving an instrument to impart rotary motion,
  b. a body, said body having:
    an outer surface,
    an inner cavity,
    a diameter, said diameter being about 0.04 to 4.0 inches, and
    at least one segment, each of said at least one segment having a segment proximal end and a segment distal end, each of said at least one flexible segment spaced from a subsequent of said at least one segment by a rigid segment,
  and
    at least one sinuous slot within at least one of said at least one segment, each of said at least one sinuous slot having:
    a depth from said outer surface to said inner surface,
    a width of about 2.5% to about 20% of said diameter,
    a ratio of amplitude to pitch in the range of about 0.1 to about 0.8,
    a helical angle of about 45 to 75 degrees from the longitudinal axis,
    a start point, said start point being a first predetermined distance from said first end, and
    an end point said point being a second predetermined distance from said first end,
  circular ends at said start point and said end point of each of said at least one sinuous slot
  said sinuous slot being cut in a helical path along a longitudinal surface of said body to form interlocking teeth, a first of said at least one sinuous slot ascending a first of said at least one flexible segment from said start point to said end point in a first direction, to create a flexible segment,
  a rigid second end, said rigid second end being dimensioned to receive a tool to receive said rotary motion from said body and transmit said rotary motion to a tool,
  wherein said rotary motion is transferred by said interlocking teeth locking with adjacent teeth to transfer said rotary motion while said body is bent about an axis.

30. The flexible shaft of claim 29 wherein at least another of said at least one sinuous slot ascends another of said at least one segment in a helical path along a longitudinal surface of said body from said start point of said another of said at least one sinuous slot to said end point of said another of said at least one sinuous slot in said first rotational direction.

31. The flexible shaft of claim 29 wherein at least another of said at least one sinuous slot ascends another of said at least one segment in a helical path along a longitudinal surface of said body from said start point of said another of said at least one sinuous slot to said end point of said another of said at least one sinus slot in a second rotational direction.

32. The flexible shaft of claim 29 wherein at least another of said at least one sinuous slot ascends said flexible segment from said start point of said another of said at least one sinuous slot in a second direction, said start point of said another of said at least one sinuous slot being spaced from said start point of said first of said at least one said sinuous slot, a first of said at least one sinuous slot and said another of said at least one sinuous slot crossing sinuous paths.

33. The flexible shaft of claim 32 wherein a first of said at least one sinuous slot ascends another of said at least one segment from said start point of said first of said at least one sinuous slot in a first rotational direction and a second of said at least one sinuous slot ascends said another of said at least one segment from said start point of said another of said at least one sinuous slot in a second rotational direction, said start point of said another of said at least one sinuous slot being spaced from said start point of said first of said at least one sinuous slot, a first of said at least one sinuous slot and another of said at least one sinuous slot crossing sinuous paths.

34. The flexible shaft of claim 29 wherein another of said at least one sinuous slot ascends said first of said at least one flexible segment from said start point of said another of said at least one sinuous slot in said first direction, said start point of said another of said at least one sinuous slot being spaced from said start point of said first of said at least one sinuous slot, said first of said at least one sinuous slot and another of said at least one sinuous slot having parallel spaced ascending paths.

35. The flexible shaft of claim 34 wherein a first of said at least one sinuous slot ascends another of said at least one segment from said start point of said first of said at least one sinuous slot in a first direction and a second of said at least one sinuous slot ascends from said start point of said second of said at least one sinuous slot in said first direction, said start point of said second of said at least one sinuous slot being spaced from said start point of said first of said at least one sinuous slot, said first of said at least one sinuous slot and said second of said at least one sinuous slot having parallel spaced ascending paths.

36. The flexible shaft of claim 29 wherein at least another of said at least one sinuous slot ascends a subsequent of said at least one flexible segment in a helical path along a longitudinal surface of said body from said start point of said another of said at least one sinuous slot to said end point of said another of said at least one sinuous slot in a second rotational direction.

37. The flexible shaft of claim 29 wherein a first of said at least one sinuous slot ascends another of said at least one segment from said start point of said first of said at least one sinuous slot in a first rotational direction, and another of said at least one sinuous slot ascends said another of said at least one segment from said start point of said another of said at least one sinuous slot in a second rotational direction, said start point of said another of said at least one sinuous slot being spaced from said start point of said first of said at least one sinuous slot, a first of said at least one sinuous slot and said another of said at least one sinuous slot crossing sinuous paths.

38. The flexible shaft of claim 29 wherein at least one of said at least one sinuous slot is at an angle with a plane tangent to the outer surface to form an undercut.

39. The flexible shaft of claim 38 wherein said angle is in the range of about one to about 75 degrees.

40. The flexible shaft of claim 38 wherein said angle is in the range of about 30 to about 45 degrees.

41. The flexible shaft of claim 29 wherein at least one of said at least one sinuous slot has a depth perpendicular to a plane tangent to the outer surface of said body.

42. The flexible shaft of claim 29 further comprising a elastomeric material, said elastomeric material applied to at least one from the group of interior cavity, sinuous slot, exterior surface, interior surface of said interior cavity.

43. The method of controlling the flexibility of a flexible shaft for a tool to transmit rotary motion comprising the steps of:
  selecting a flexible shaft, said flexible shaft having at least one sinuous slot in a helical pattern cut in a helical path along a longitudinal surface of said shaft to form interlocking teeth, said at least one sinuous slot ascending said at least one flexible segment from a segment start point to a segment end point,
  attaching an instrument to a first end of said flexible shaft,
  attaching a tool to a second end of said flexible shaft,
  flexing said shaft to place said tool in an element to receive said rotary motion,
  rotating said instrument,
  transmitting said rotary motion from said instrument to said tool along said flexible shaft to said tool.

* * * * *